United States Patent
Heltai

(10) Patent No.: US 8,702,776 B2
(45) Date of Patent: Apr. 22, 2014

(54) METHOD FOR DEPLOYING A SLEEVE AND TUBING DEVICE FOR RESTRICTING AND CONSTRICTING ANEURYSMS AND A SLEEVE AND TUBING DEVICE AND SYSTEM

(71) Applicant: Paul Heltai, Boca Raton, FL (US)

(72) Inventor: Paul Heltai, Boca Raton, FL (US)

(*) Notice: Subject to any disclaimer, the term of this patent is extended or adjusted under 35 U.S.C. 154(b) by 4 days.

(21) Appl. No.: 13/846,037

(22) Filed: Mar. 18, 2013

(65) Prior Publication Data

US 2013/0218191 A1 Aug. 22, 2013

Related U.S. Application Data

(63) Continuation-in-part of application No. 13/087,420, filed on Apr. 15, 2011, now abandoned.

(60) Provisional application No. 61/366,726, filed on Jul. 22, 2010, provisional application No. 61/327,982, filed on Apr. 26, 2010.

(51) Int. Cl.
*A61F 2/06* (2013.01)
(52) U.S. Cl.
USPC .......................................................... 623/1.1
(58) Field of Classification Search
USPC .................................................. 623/1.1, 1.25
See application file for complete search history.

(56) References Cited

U.S. PATENT DOCUMENTS

| | | | |
|---|---|---|---|
| 4,493,711 A * | 1/1985 | Chin et al. ................. | 604/271 |
| 5,534,024 A | 7/1996 | Rogers et al. | |
| 5,593,418 A * | 1/1997 | Mollenauer ................ | 606/192 |
| 5,607,443 A * | 3/1997 | Kieturakis et al. .......... | 606/192 |
| 6,030,392 A | 2/2000 | Dakov | |
| 6,293,968 B1 * | 9/2001 | Taheri ........................ | 623/1.15 |
| 6,599,302 B2 | 7/2003 | Houser et al. | |
| 7,818,084 B2 | 10/2010 | Boyden et al. | |
| 2004/0098104 A1 | 5/2004 | Sirhan et al. | |
| 2004/0147803 A1 | 7/2004 | Hegde et al. | |
| 2006/0069426 A1 | 3/2006 | Weinberger | |
| 2006/0281966 A1 * | 12/2006 | Peacock ..................... | 600/37 |
| 2007/0135904 A1 * | 6/2007 | Eidenschink et al. ...... | 623/1.35 |
| 2008/0133040 A1 | 6/2008 | Boyden et al. | |
| 2008/0188923 A1 | 8/2008 | Chu | |
| 2008/0294237 A1 | 11/2008 | Chu | |
| 2009/0024152 A1 | 1/2009 | Boyden et al. | |

OTHER PUBLICATIONS

Chang et al., "Enabling Sutureless Vascular Bypass Grafting With the Exovascular Sleeve Anastomosis", Journal of Vascular Surgery, vol. 32, No. 3, Sep. 2000, pp. 524-530.

* cited by examiner

*Primary Examiner* — Andrew Iwamaye
*Assistant Examiner* — Leslie Coburn
(74) *Attorney, Agent, or Firm* — Laurence A. Greenberg; Werner H. Stemer; Ralph E. Locher

(57) ABSTRACT

A sleeve device, system and method are provided for restricting and/or constricting aneurysms. More particularly, a sleeve and/or a double-walled sleeve is located in or on a vessel in the location of an aneurysm. When placed around the outside of a vessel, is used to restrict and/or constrict the aneurysm containing portion of the vessel. If desired, the sleeve may be constructed as a double-walled sleeve that can be inflated to apply pressure to and/or in the vessel.

20 Claims, 18 Drawing Sheets

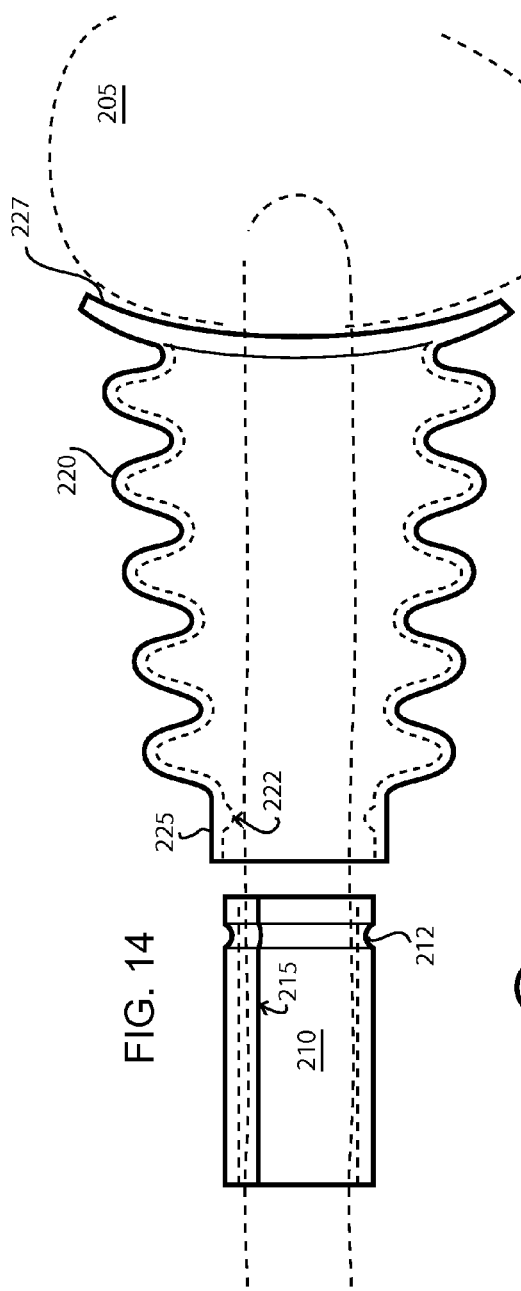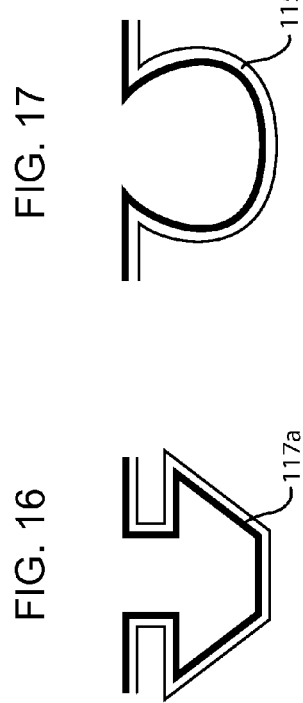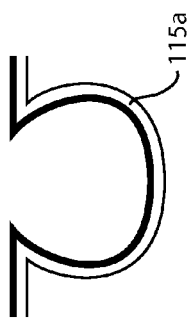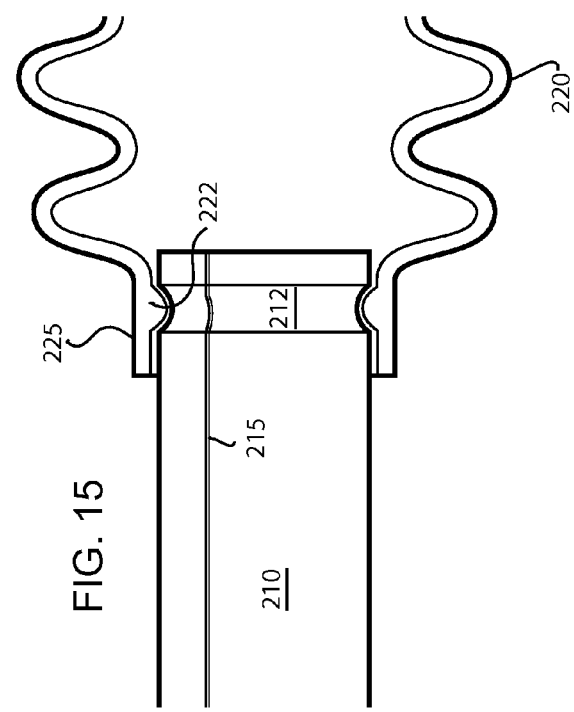

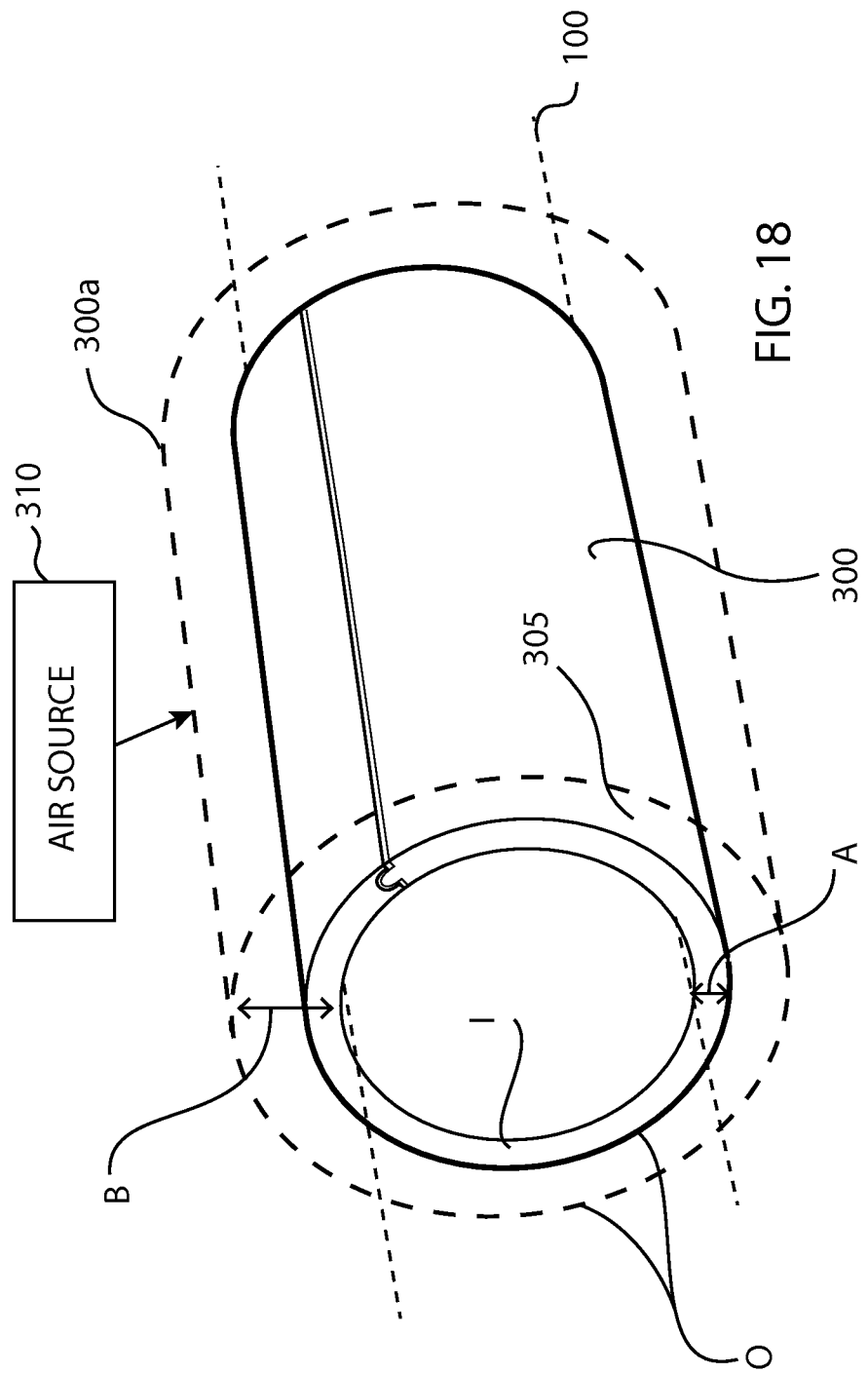

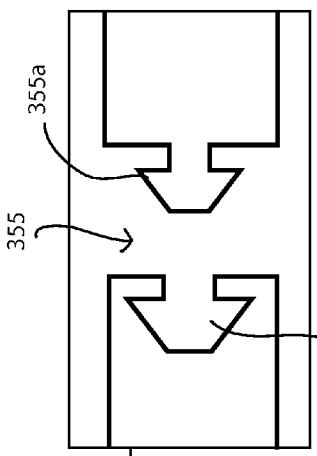
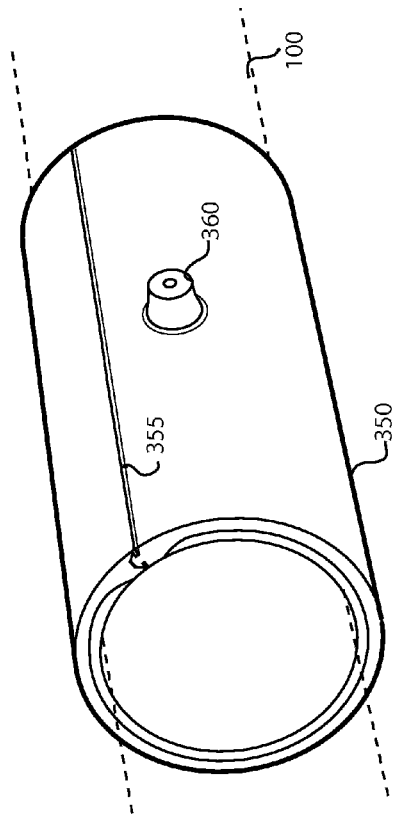
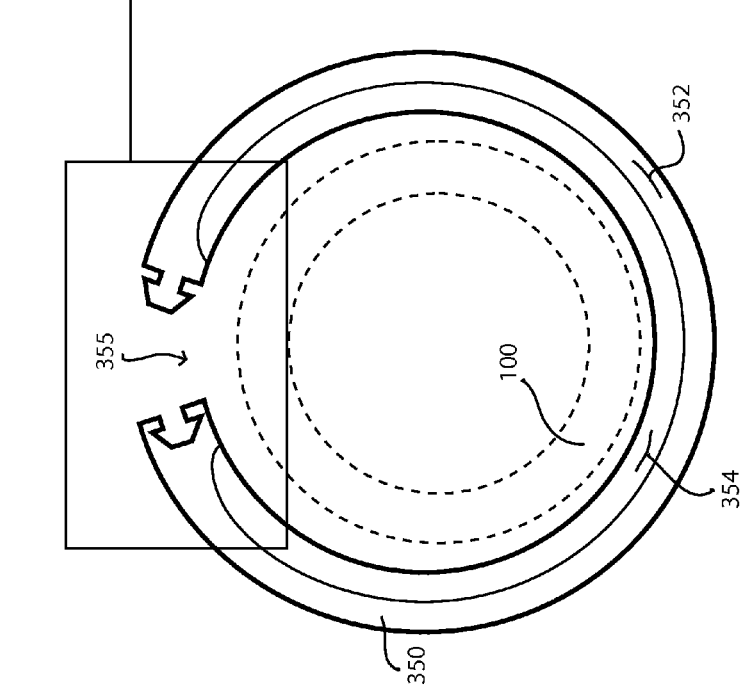

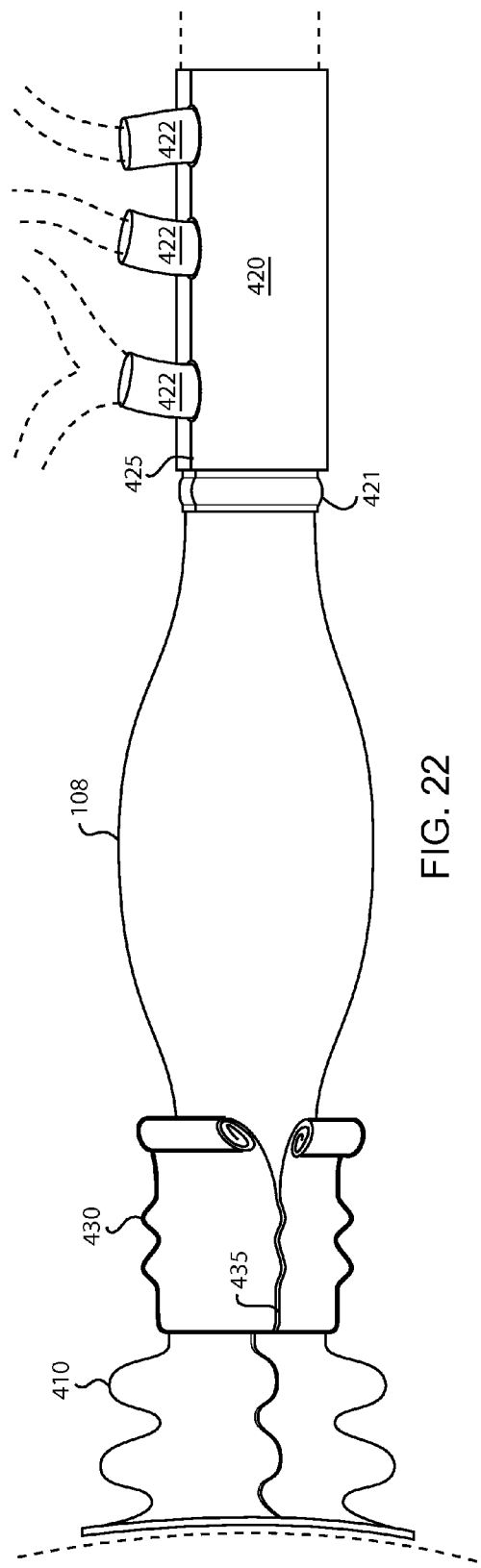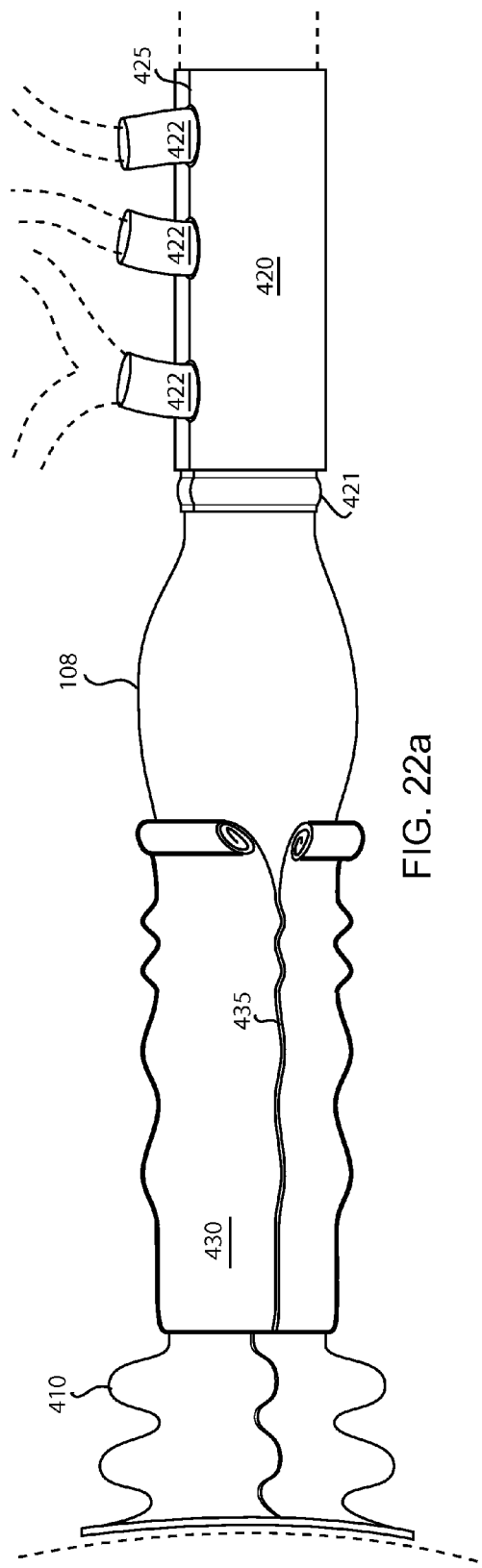

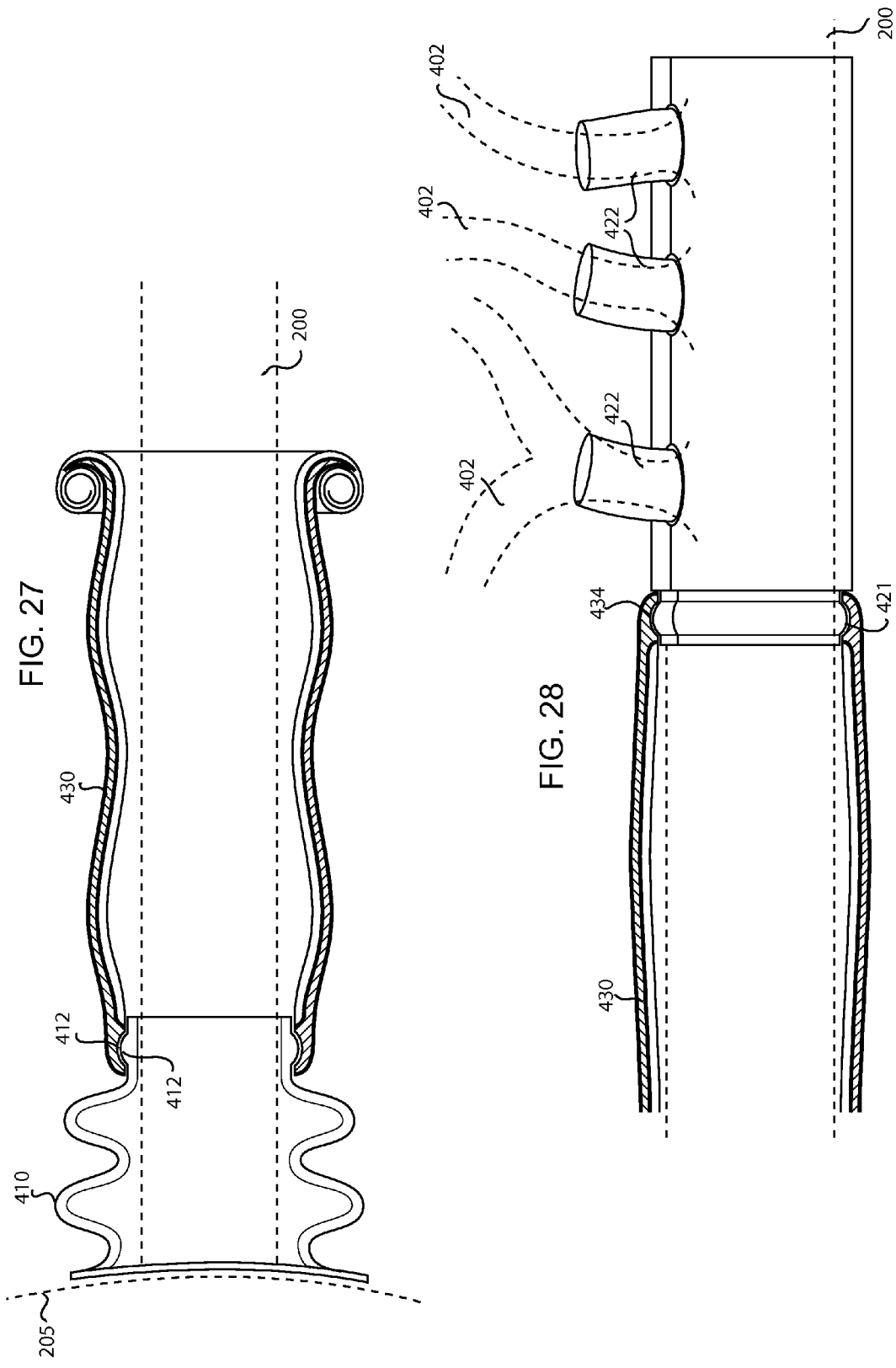

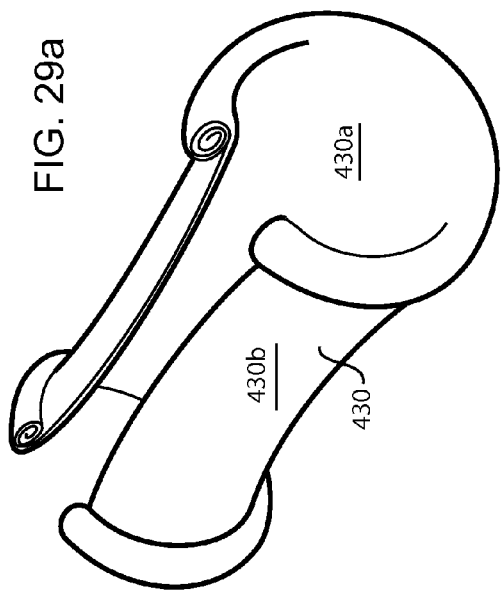
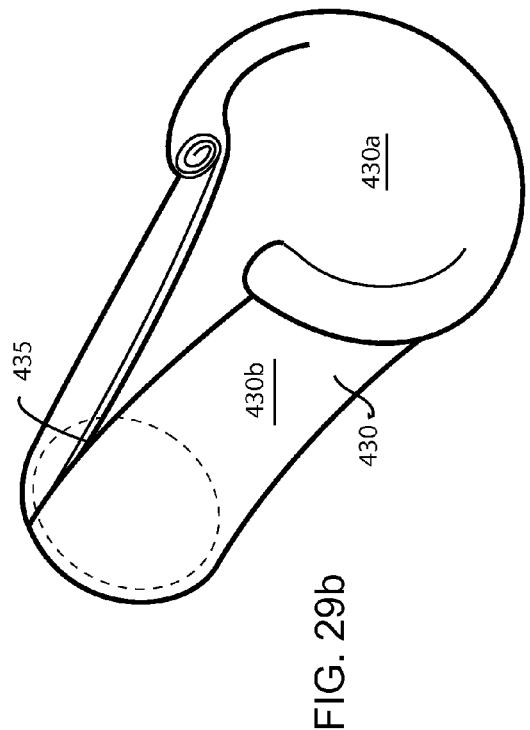
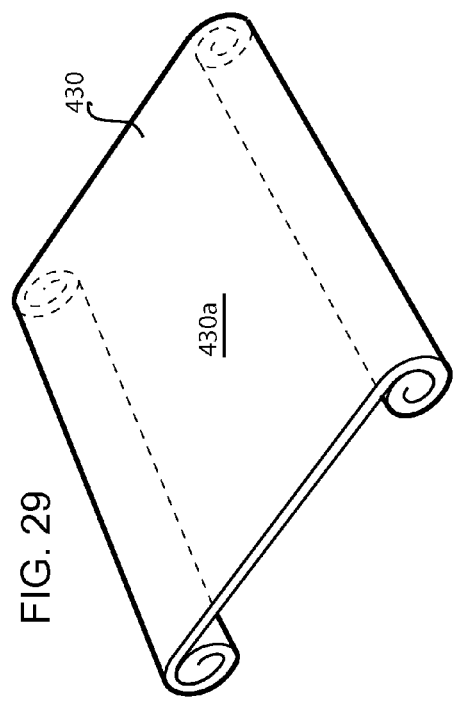

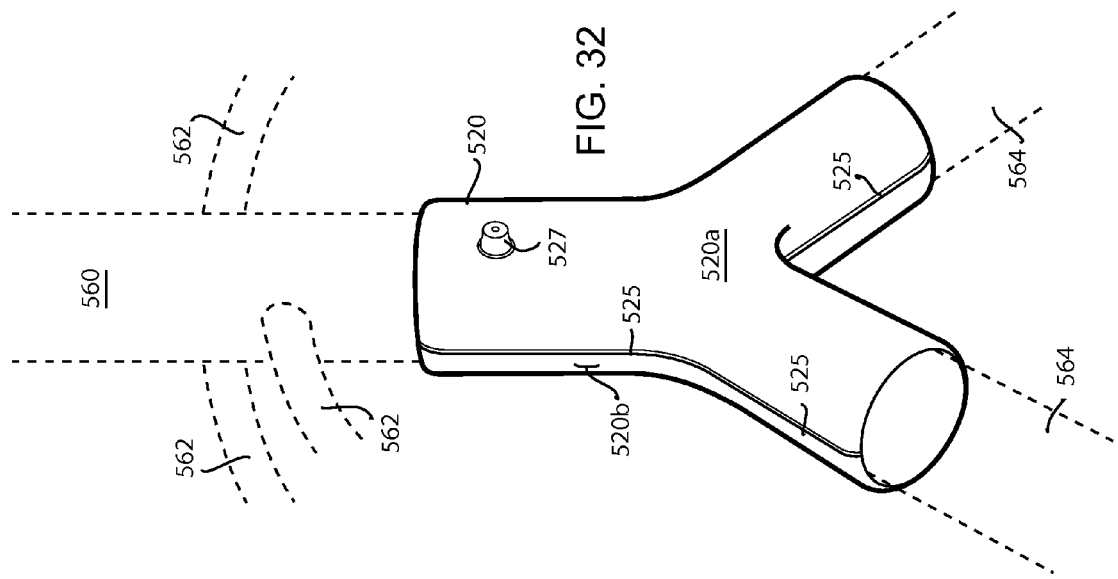
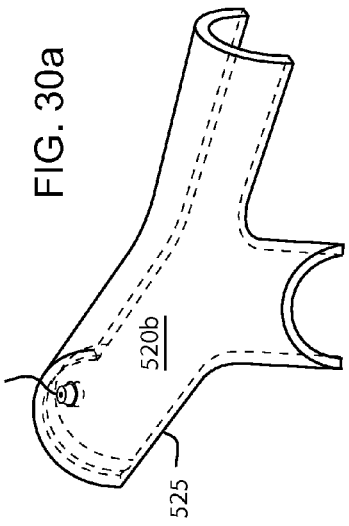
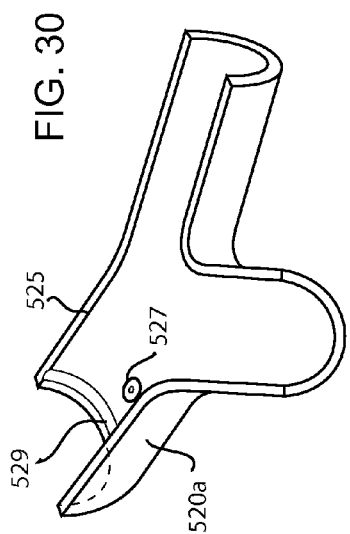
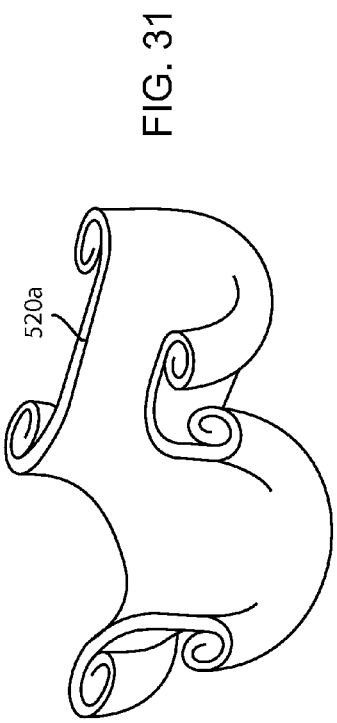

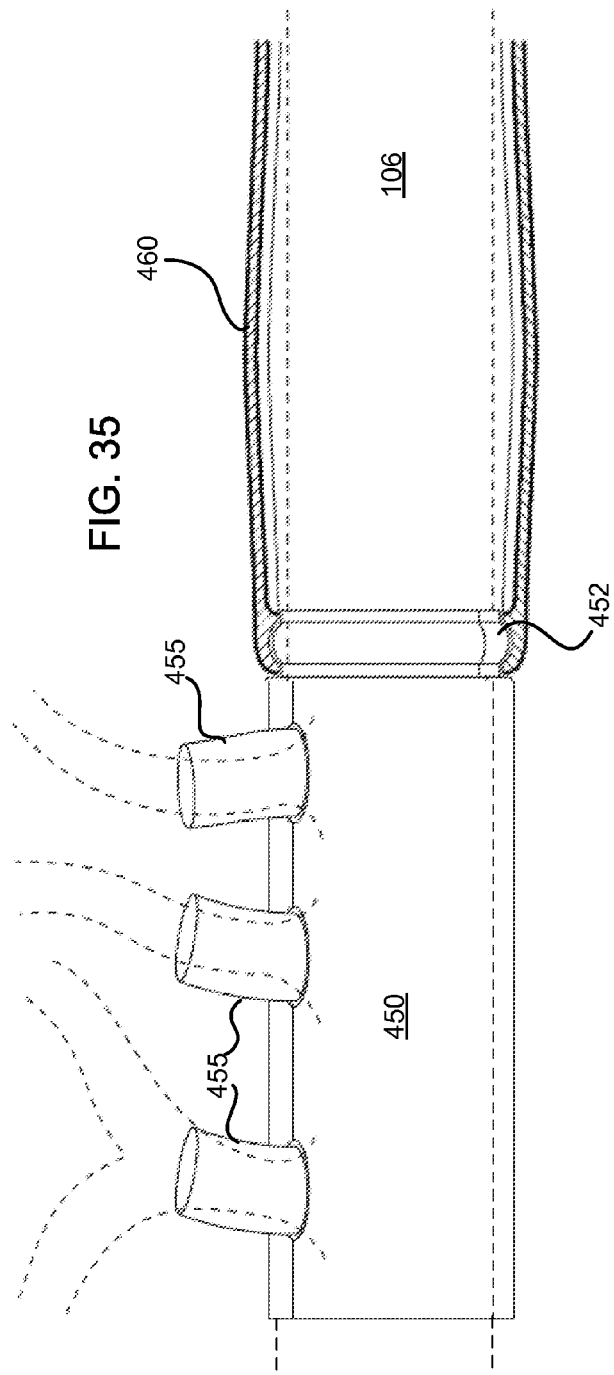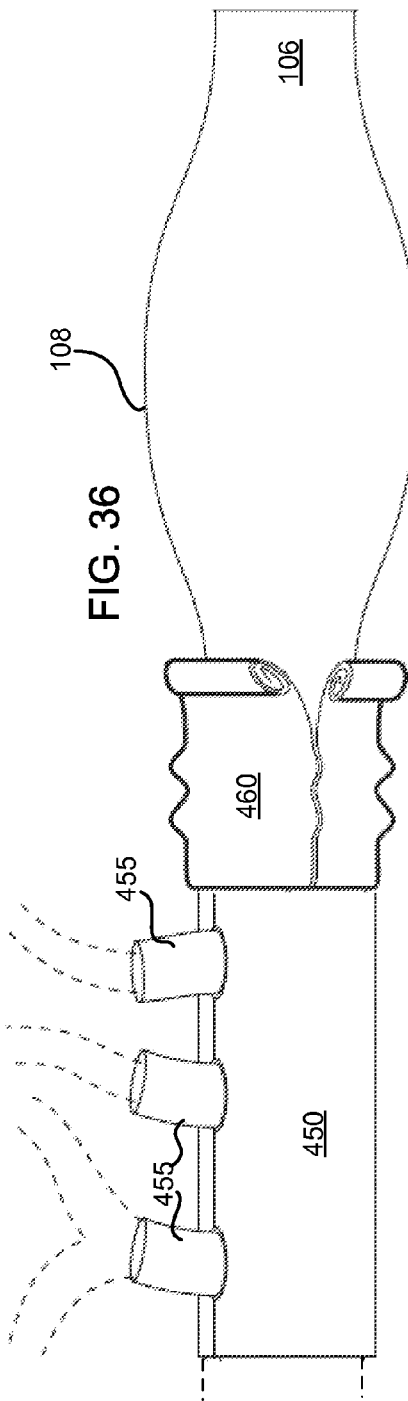

METHOD FOR DEPLOYING A SLEEVE AND TUBING DEVICE FOR RESTRICTING AND CONSTRICTING ANEURYSMS AND A SLEEVE AND TUBING DEVICE AND SYSTEM

CROSS-REFERENCE TO RELATED APPLICATIONS

The present application is a continuation-in-part of co-pending U.S. patent application Ser. No. 13/087,420, filed Apr. 15, 2011, entitled "Sleeve and Tubing Device for Restricting and Constricting Aneurysms and a System and Method for Using Such a Device", which claimed priority from Provisional Patent Application No. 61/366,726, filed on Jul. 22, 2010, entitled "Restricting and Constricting Aneurysms Sleeve Inflating Tubing Device"; and from Provisional Patent Application No. 61/327,982, filed on Apr. 26, 2010, those applications being incorporated herein, by reference, in their entireties.

BACKGROUND OF THE INVENTION

1. Field of the Invention

A system, device and method for constricting aneurysms using a sleeve are provided.

2. Description of the Related Art

The treatment of aneurysms poses an operating problem, marked by high risk, high rates of death, long surgical procedure and a long recovery time.

An aneurysm is a bulge, a hernia of an artery. There are several types of aneurysm locations on an aorta: ascending, descending, thoracic and abdominal aortic aneurysms.

Surgical Repair of Aortic Aneurysms

Any aortic aneurysms that are large, causing symptoms or rapidly getting bigger are considered at risk of rupturing. Surgery is usually recommended if any one of these factors is present.

Both traditional surgery and endovascular aortic repair are used to treat aortic aneurysms. If surgery is needed, the doctor will make a large cut in the chest or abdomen. Then, the aneurysm will be removed and the damaged portion of the aorta will be replaced with a man-made graft. Some aortic aneurysms can be repaired without traditional surgery, using endovascular aortic repair. A stent graft is inserted through an artery in the groin. The stent graft makes a bridge between the healthy parts of the aorta (above and below the aneurysm).

At the present time, for any aortic aneurysms, a doctor will recommend surgery based on the following guidelines:

a. If the aneurysm is located where the aorta ascends up out of the heart, surgery is recommended when it reaches 5.5 to 6.0 cm in diameter.

b. If the aneurysm is located where the aorta begins to descend, surgery is recommended when it reaches 6.0 cm in diameter.

c. In those with Marfan's syndrome, surgery is recommended when the aneurysm reaches 5.5 cm in diameter.

d. If the aneurysm causes significant aortic regurgitation, surgery is recommended.

e. If the aneurysm is located in the thoracic or abdominal region, surgery is recommended when it reaches 5.5 to 6.0 cm in diameter.

f. The aorta is the major artery which arises from the heart. It carries all the blood that is pumped out of the heart and distributes it via its many branches to all the organs of the body. The aorta is divided into four portions: 1) the ascending aorta, 2) the aortic arch, 3) the descending aorta, 4) the thoracic aorta, and 5) the abdominal aorta.

Surgeons and institutions around the world have differing experiences with aortic aneurysms and may follow different protocols in the treatment of the disease.

If surgery is chosen, the doctor will evaluate the overall health, including assessments of the heart, lungs, and circulatory system, the kidneys, and the gastrointestinal system. The decision whether to have surgery is based on the outcome of these evaluations. The risk of death or injury during the operation increases if other disease is present.

If the evaluation of the heart indicates that the patient has significant heart disease, the patient should undergo coronary artery bypass surgery (CABG) or coronary angioplasty prior to repairing an aortic aneurysm. This is because coronary artery disease is the most important underlying factor contributing to complications, such as heart attack, in the period before and after the operation. Other complications, such as stroke and infection of the graft, can also occur.

Kidney disease, chronic lung disease, and cirrhosis of the liver may raise the risk of death and complications during the operation.

Smoking and high blood pressure put a person at a higher risk for complications from surgery. They are also risk factors for the rupture of any aneurysms.

It is not an option to wait until an aneurysm has ruptured before surgery is done. Most people who have a ruptured aortic aneurysm die. Surgery for a ruptured aneurysm is dangerous because of the large amount of blood loss.

Two types of surgery are presently performed on aortic aneurysms:

1. The Traditional Surgery:

The affected portion of the Aorta is completely removed and replaced by a Dacron Tubing. The Dacron Tubing is stitched in different places. Many times, the stitches do not hold and one or more new operations need to be done.

2. Endovascular Aortic Repair:

The surgery is performed inside the aorta using thin, long tubes called stents. Through small incisions in the groin, the stents are used to guide and deliver a stent-graft through the blood vessels to the site of the aneurysm. The stent graft is then deployed in the diseased segment of the aorta.

An endovascular stent graft is a fabric tube supported by metal wire stents (also called a scaffold) that reinforces the weak spot in the aorta. By sealing the area tightly with the artery above and below the aortic aneurysm, the graft allows blood to flow through it without putting pressure on the aneurysm.

Endovascular repair of abdominal aneurysms is generally less painful and has a lower risk of complications than traditional surgery because the incisions are smaller. Endovascular aorta aneurysm procedures also allow a patient to leave the hospital sooner and make a faster recovery. However, possible complications of endovascular repair include:

Leaking of blood around the graft, known as "endoleak";

Movement, or migration, of the graft away from its initial placement; and

Stent fracturing.

Additional complications that are rare but serious include:

Paralysis;

Delayed rupture of the aneurysm; and

Infection.

The long-term durability of endovascular stent grafting to treat an abdominal aneurysm is yet unknown because this is a fairly new procedure. For this reason, patients who have endovascular repair of their thoracic aneurysms must be monitored closely on a regular basis with examinations and imaging studies.

Blood vessel sleeves are known. U.S. Pat. No. 7,818,084 to Boyden et al discloses a method and system for making a blood vessel sleeve having dimensions based on blood vessel data from an individual, while U.S. Patent Application Publication No. 2008/0133040 to Boyden et al discloses methods and systems for specifying a blood vessel sleeve. Similarly, U.S. Patent Application Publication No. 2009/0024152 to Boyden et al., discloses a custom-fitted blood vessel sleeve.

Additionally, U.S. Patent Application Publication No. 2008/0188923 to Chu discloses methods and systems for preventing aneurysm rupture and reducing the risk of migration and endoleak, wherein an inflatable multiple wall liner is applied directly to treat the interior of the aneurysm site. U.S. Pat. No. 6,599,302 to Houser et al., discloses a system and components for treating aortic aneurysms including a reinforcing graft and fittings for securing the graft to a host vessel and to branch vessels. In Houser, combinations of fittings and rings or other compression mechanisms secure vessels or grafts frictionally, for end-end or end-side couplings.

Further, an article entitled "Enabling Sutureless Vascular Bypass Grafting With The Exovascular Sleeve Anastomosis" by D. W. Chang, et al., (J. Vasc. Surg.) (2000) 32:524-530, disclosed the use of an exovascular sleeve bypass graft that is drawn over an artery and secured in place with a cable tie.

What is needed is a simplified device, system and method for preventing an aneurysm in the walls of a vessel containing from growing or expanding and/or for restricting and/or constricting the walls of a vessel containing an aneurysm. What is additionally needed is a blood vessel sleeve device and system that can remain localized to a desired location and does not, itself, cause damage or chafing to the vessel or associated organs.

SUMMARY OF THE INVENTION

In order to meet the foregoing needs, as well as to overcome disadvantages of the heretofore-known methods and devices of this general type, it is accordingly an object of the invention to provide a sleeve and tubing device for preventing an aneurysm from growing or expanding and/or for restricting and/or constricting aneurysms and a system and method for using such a device. In one particular embodiment of the invention, a sleeve is placed on the outside of the vessel exhibiting the aneurysm, wherein it is fixed in the desired location by being anchored to a geometrical fixture of the vessel. In another particular embodiment of the invention, the sleeve placed over the aneurysm includes a bellows to reduce chafing during pulsating of the vessel. In a further embodiment of the invention, the sleeve is inflatable around the outside of the vessel, in situ. In yet a further embodiment of the invention, an inflatable sleeve is secured inside a vessel at the site of an aneurysm, and inflated, in situ.

Although the invention is illustrated and described herein as embodied in a sleeve and tubing device for restricting and constricting aneurysms, and a system and method for using such a device, it is nevertheless not intended to be limited to the details shown. Various modifications and structural changes may be made to the embodiments described herein, without departing from the spirit of the invention and within the scope and range of equivalents of the claims.

The construction of the invention, however, together with the additional objects and advantages thereof will be best understood from the following description of the specific embodiments when read in connection with the accompanying drawings.

BRIEF DESCRIPTION OF THE SEVERAL VIEWS OF THE DRAWING

FIG. 14 is a side plan, exploded view of a sleeve and bellows configuration in accordance with one particular embodiment of the invention;

FIG. 15 is a partial, side plan view of a sleeve and bellows configuration in accordance with one particular embodiment of the invention;

FIGS. 16 and 17 are partial views of keystone and dovetail locking mechanisms, respectively, made in accordance with particular embodiments of the present invention;

FIG. 18 is a perspective view of a double-walled or inflatable sleeve made in accordance with one particular embodiment of the present invention;

FIG. 19 is a longitudinal, cross-sectional view of a double-walled sleeve made in accordance with one particular embodiment of the invention;

FIG. 19a is a partial, enlarged view of the locking mechanism shown in FIG. 19;

FIG. 20 is a perspective view of a double-walled or inflatable sleeve made in accordance with another particular embodiment of the present invention;

FIGS. 22, 22*a* and 23 are representative views showing a sleeve in accordance with one particular embodiment of the invention illustrated at different stages of installation (deployment) over an aneurysm;

FIGS. 27 and 28 are representative views showing different stages of deployment of a sleeve in accordance with one particular embodiment over an aneurysm;

FIGS. 29, 29*a* and 29*b* are helpful in understanding the process of assembling (i.e., deploying and closing) a tubular sleeve from an open or flat sleeve portion, in accordance with one particular embodiment of the present invention;

FIGS. 30, 30*a* and 31 show a sleeve portion configured for use in connection with abdominal aortic aneurysms, in accordance with one particular embodiment of the present invention;

FIG. 32 shows a perspective view of one particular embodiment of an inflatable sleeve deployed and installed at a desired position relative to an abdominal aortic aneurysm;

FIGS. 35-36 show a side cut-away view and a side plan view, respectively, of one particular embodiment of the invention useful for treating a descending aortic aneurysm;

DESCRIPTION OF THE PREFERRED EMBODIMENTS

Figure 3:
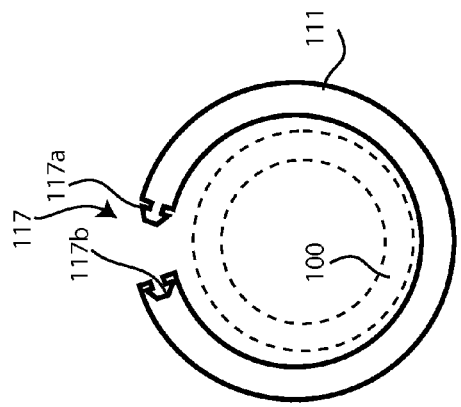
FIG. 3 is a longitudinal, cross-sectional view of a sleeve in accordance with another particular embodiment of the invention.
Figure 4:
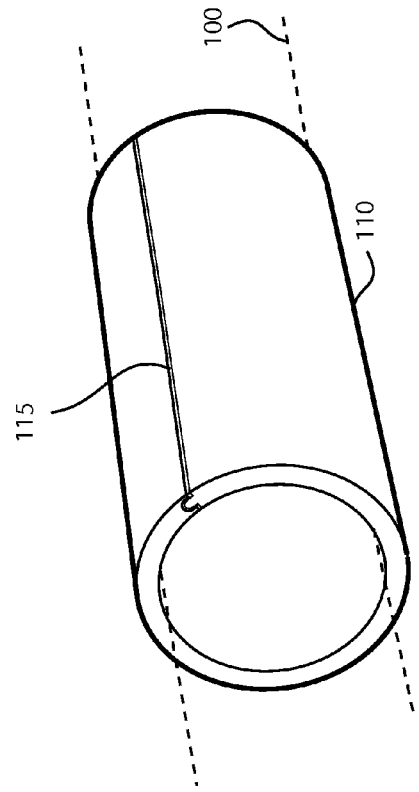
FIG. 4 is a perspective view of the sleeve of FIG. 2.
Figure 2:
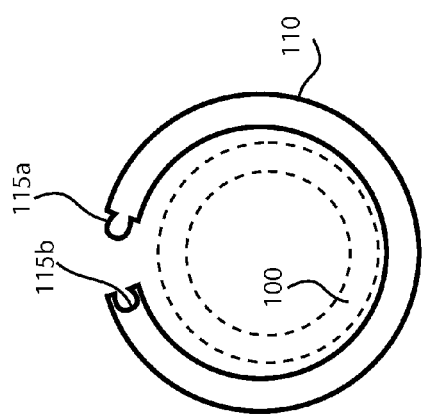
FIG. 2 is a longitudinal, cross-sectional view of a sleeve in accordance with one particular embodiment of the invention.

Referring now to FIGS. 2-4, there is shown a sleeve 110 encapsulating a vessel 100 (shown in dotted line) that contains an aneurysm. In general, the sleeve 110 is formed very simply as a round tube that can be fitted over a vessel 100 and an aneurysm contained in that vessel 100. Such a sleeve 110 may be made of any biocompatible material presently known, or to be developed in the future, such as, but not limited to, DACRON®, plastic biocompatible materials, metal biocompatible materials, composite material, or any other materials that can be used for the present purpose in the body.

Figure 1:
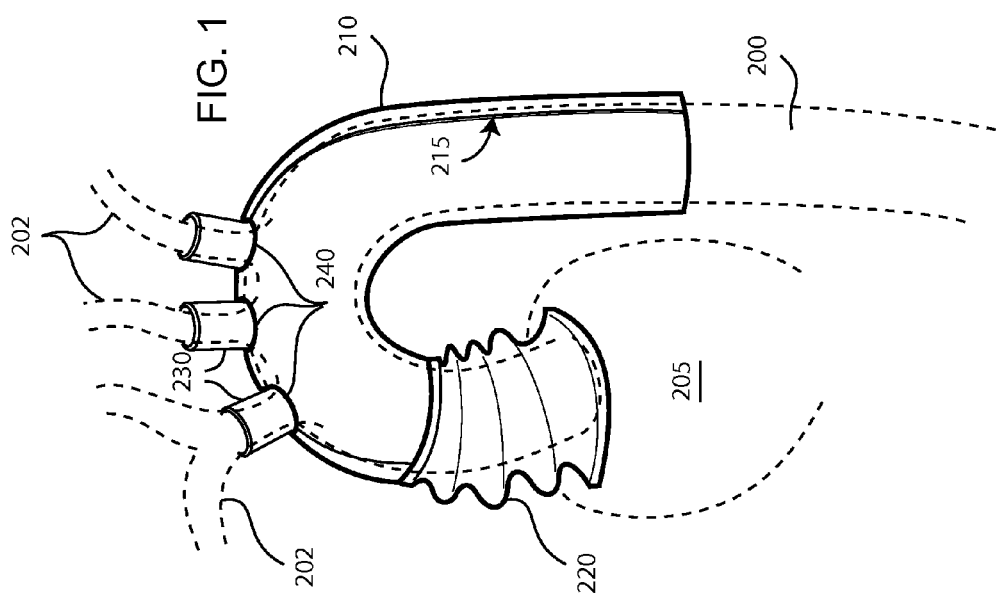
FIG. 1 is a diagrammatic view of a sleeve in accordance with one particular embodiment of the invention.

The sleeve 110 is designed to encapsulate the vessel 100, including any portion containing the aneurysm, and thus, is configured to closely approximate the vessel 100. Note that, the sleeve 110 can be adapted for use with any vessel, and configured to conform to the particular anatomy of the vessel on which it is to be used. For example, FIG. 1 shows an aneurysm sleeve 210 adapted to surround a patient's aorta 200 (shown in dotted line), and which includes, in accordance with one particular embodiment of the invention, a bellows, sleeves, and saddle sleeves provided over and around an ascending and descending aortic aneurysm.

Referring back to FIGS. 2-4, the sleeve 110 for encapsulating an aneurysm containing vessel 100 is provided. The sleeve 110 is formed as a sheet that can be rolled around the vessel 100, from a location external to the vessel 100, and locked together around the vessel 100, by engaging the locking mechanism 115. Locking mechanism 115 of FIGS. 2-4 includes interlocking, mating portions 115*a* and 115*b* (FIG. 2) or 117*a* and 117*b* (FIG. 3) that extend the length of the sleeve 110 and which mate to lock the sleeve 110 in the previously described form of a round tube.

In one particular embodiment of the invention, shown in FIGS. 2, 4 and 17, the locking mechanism 115 includes an interlocking male tongue 115*a* and female groove 115*b*, or "angular omega", locking configuration that snap together to form the round tube around the affected vessel. In another particular embodiment of the invention shown in FIGS. 3 and 16, a keystone or dovetailed configuration is used, wherein a male dovetail 117*a* interlocks (i.e., mates or "snaps together") with a female dovetail 117*b* to secure the sleeve 110, 111 as a round tube and to prevent reopening of the sleeve 110, 111 after installation. The same interlocking systems 115, 117 can be used in connection with any tube, sleeve and/or saddle sleeve described herein. Note that, the foregoing is not meant to be limiting, as other mechanisms for locking the sleeve 110, 111 into a tube can be used. For example, if desired, any other locking mechanism, including, but not limited to, gluing, stitching, snap-fitting, etc., may be used to secure and maintain the sleeve 110, 111 in the form of a tube after installation.

Figure 7:
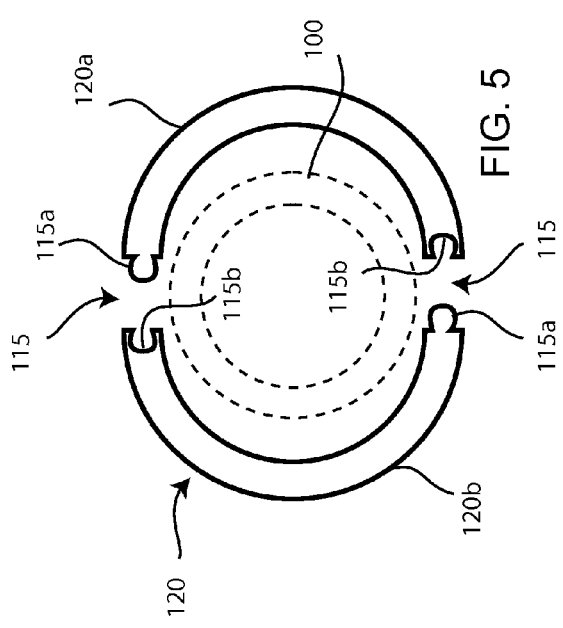
FIGS. 7 and 8 are perspective views of sleeves made in accordance with other embodiments of the instant invention.
Figure 8:
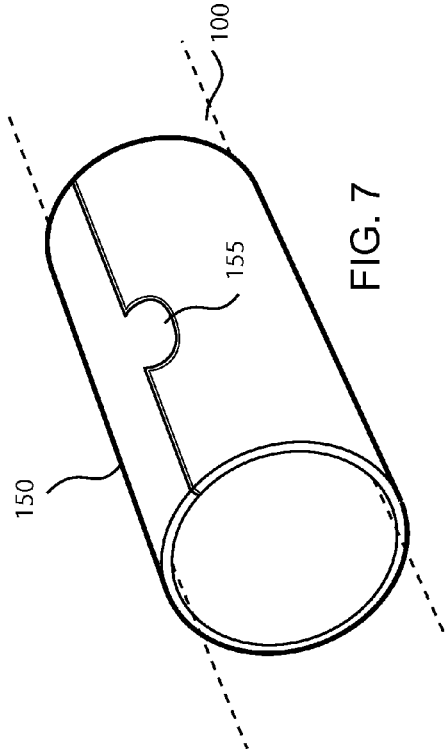

FIGS. 7 and 8 show further alternate embodiments of a sleeve 150, 160 in accordance with the present invention, including an interlocking key or tab locking mechanism 155, 165, respectively, for ensuring that the locking mechanisms 155 and 165 of sleeves 150, 160, remain securely closed, once connected around the vessel 100.

Figure 5:
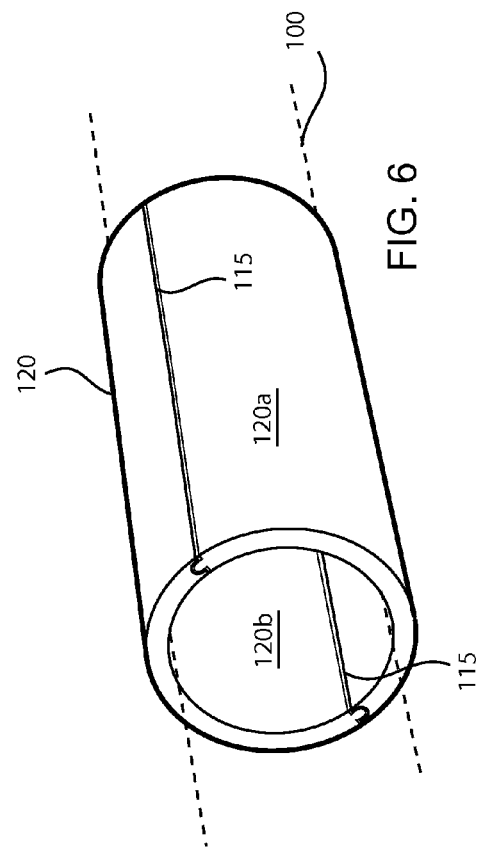
FIG. 5 is an exploded view of a sleeve made in accordance with a further embodiment of the instant invention.
Figure 6:
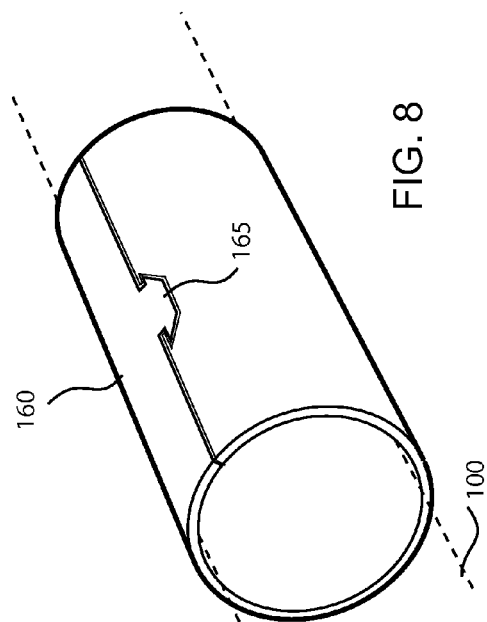
FIG. 6 is a perspective view of the sleeve of FIG. 5.

If desired, a sleeve 110, 111, 150, 160 can be subdivided into two or more parts, instead of the single interlocking part shown in FIGS. 2-4. For example, referring more particularly in FIGS. 5-6, a sleeve 120 can be made in two halves 120*a* and 120*b*, which are matingly engaged about the vessel 100, through the use of two locking mechanisms 115 or 117 (not shown in FIGS. 5-6).

The locking mechanisms 115, 117, 125, 155, 165 of FIGS. 2-8 are initially open, to permit sleeve placement, and can be snapped closed to secure the sleeves 110, 111, 120, 150, 160, respectively, over and around the affected vessel, thus forming a sleeve having the geometrical configuration of the vessel to be to be repaired and/or mended.

For example, referring now to FIG. 1, in the case of an ascending and/or descending aneurysm, the sleeve 210 of FIG. 1, will take the shape, the geometrical configuration, and the curvature of the aorta and the ascending and/or descending aneurysm, as it is unfolded and deployed over and around the affected aortic aneurysm. Similarly, in the case of a thoracic aneurysm, the sleeve 430 of FIGS. 29, 29a, 29b, or in the case of an abdominal aneurysm, the sleeves 520, 520a, and 520b of FIGS. 30, 30a, 31, 32, 34, will take the shape, the geometrical configuration, and the curvature of the aorta and the aneurysm, as it is unfolded and deployed over and around the affected aortic aneurysm.

Referring more particularly to FIG. 1, the sleeve 210 is placed over and around (i.e., surrounds or encapsulates) the affected portion of the particular aorta to stop the aneurysm from growing or expending. In addition to surrounding the portion of the aorta containing the aneurysm, the sleeve 210 should additionally extend beyond the affected portion of the particular aorta. The sleeve 210 of FIG. 1 can include a locking mechanism 215 extending the length thereof, as described more particularly in connection with FIGS. 2-8, or even another type of locking mechanism, such as glue or stitching. Further, the sleeve 210 can interface with saddle sleeves or "securing buttons" 230 to surround at least a portion of one or more vessels branching off from the affected aorta 200. The saddle sleeves 230 can be provided as either separate sleeves (i.e., separate "saddle" sleeves or "securing buttons" 235, 237 of FIGS. 10 and 11), or as part of a three branch manifold (250 of FIGS. 9, 12 and 13) having three saddle sleeves 252.

Figure 9:
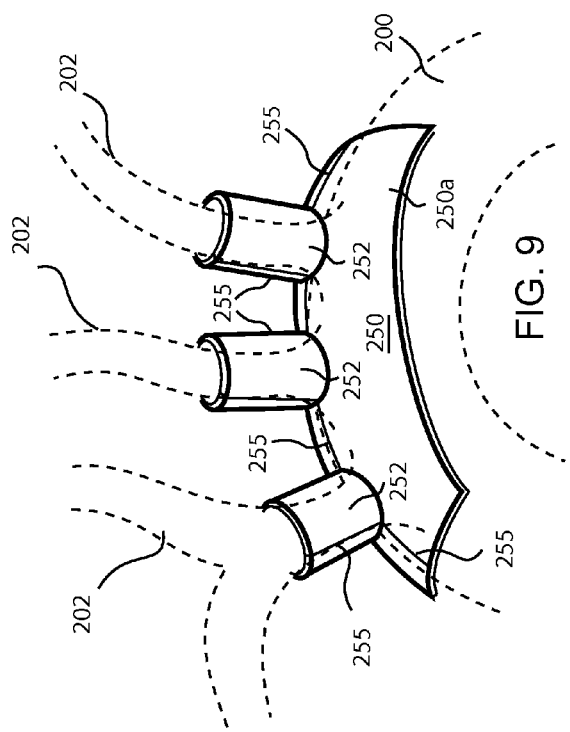
FIG. 9 is a perspective view of three-branch manifold for use with one particular embodiment of the present invention.
Figure 13:
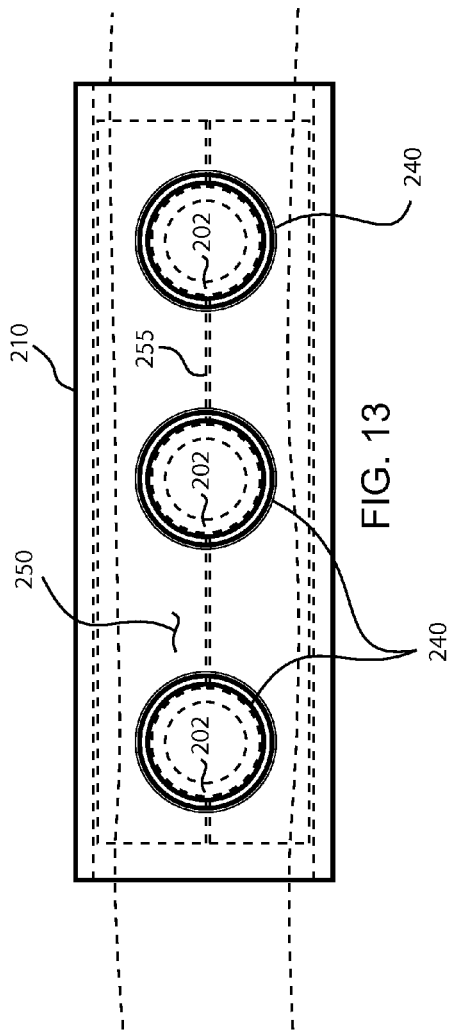
FIG. 13 is a top plan view of a three-branch manifold, in accordance with the manifold of FIG. 9, overlaid with a securing sleeve, in accordance with one particular embodiment of the invention.

More particularly, referring now to FIGS. 1, 9 and 13, it can be seen that, in one particular embodiment of the invention designed for use with an ascending aortic aneurysm, the sleeve 210 can include, formed therein, one or more openings 240 to permit the three branching arteries 202 of the aorta 200 to exit the sleeve 210. More particularly, a saddle sleeve 230, 235, 237, 252 can be provided around each of the three branching arteries extending from the ascending aorta. As can be seen, a longitudinal axis defined through each of the saddle sleeves 230 is disposed substantially perpendicular to a longitudinal axis through the sleeve 210 at the point where the saddle sleeve 230 intersects the sleeve 210. If desired and/or applicable, the longitudinal axis defined through the saddle sleeves 230 could be disposed at some other, non-zero angle relative to the axis through the sleeve 210 at the point of intersection of the two sleeves 210, 230.

Figure 10:
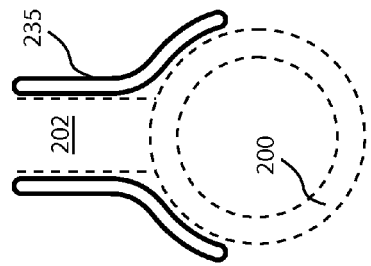
FIG. 10 is a longitudinal, cross-sectional view of a vessel carrying an additional saddle sleeve or securing button in accordance with one particular embodiment of the invention.
Figure 11:
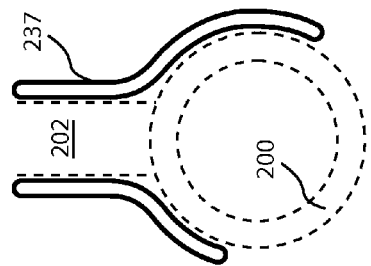
FIG. 11 is a longitudinal, cross-sectional view of a vessel carrying an additional saddle sleeve or securing button in accordance with another particular embodiment of the invention.

For example, in one particular embodiment of the invention, a saddle sleeve or "securing button" of a type shown in FIGS. 10 and 11 can be secured about one or more of the arteries 202 extending from the aorta 200, using a locking mechanism running longitudinally along the entire length of the saddle sleeve, such as the locking mechanisms 115, 117, 155, 165 of FIGS. 2-8, or some other form of locking mechanism that permits securing the securing or saddle sleeve together about the arteries 202.

In another particular embodiment of the invention shown in FIGS. 1, 9, 12 and 13, a three branch manifold can be secured at a desired position relative to the arteries 202 using a locking mechanism 255, which may be used to snap together two halves 250a and 250b around the arteries 202. FIG. 13 shows such a manifold 250 (in dotted line) located below a sleeve 210, which may, alternately, be a "securing" sleeve, as will be described hereinbelow in connection with the "securing" sleeve 420 of FIGS. 22, 22a and 23.

Each of the saddle sleeves 235, 237, 252 includes at least one locking device, as discussed more particularly hereinabove in connection with FIGS. 2-8 or any other locking, gluing, stitching device or system to secure the portions of the saddle sleeves 235, 237, 252 in tubular form. When used in connection with a three branch manifold, such as is shown in FIG. 9, it should be understood that the saddle sleeves 252 are integral with the body of the manifold, and thus, the locking mechanisms for the saddle sleeves 252 can be the same as, part of, and/or in alignment with, the locking mechanism 255 for the body of the manifold 250.

Once the saddle sleeves 235, 237 are engaged around the vessels 202, or the three branch manifold 250 is engaged over the aorta 200 with each of the securing sleeves 252 secured around a vessel 202, the sleeve 210 can be engaged around the ascending aorta 200, as shown more particularly in FIG. 1. In particular, a sleeve 210 overlays at least a portion of the saddle sleeves 235, 237 or the three branch manifold 250, as shown more particularly in FIGS. 12 and 13, in order to maintain the saddle sleeves 235, 237, 252 at a desired location relative to the vessels 202 and the aorta 200, and provides a buffer around the artery or vessel 202, under the sleeve 210.

The saddle sleeves 235, 237 and/or of the saddle sleeves 252 of the three branch manifold 250 have two main functions. First, they help anchor the sleeve 210, stopping it from sliding up or down along the ascending aorta. Second, they allow the sleeve 210 to move up and down without the risk of chaffing, scraping and/or otherwise damaging the walls of the arteries 202.

When used in a ascending or descending aortic aneurysms and/or for a thoracic aortic aneurysm and an abdominal aortic aneurysm, the saddle sleeves 235, 237 will be "saddle-shaped", in order to be saddled over the aorta 200. In particular, the "saddle portion" of a saddle sleeve or securing button 235, 237 will be used wherever it is necessary, at the intersection of any branching arteries, in the manner shown in FIGS. 10, 11 and 12. As indicated hereinabove, such a "saddle" shape will permit the up and down movement of the aorta, without the risk of chaffing, scraping, and/or damaging the walls of the aorta The saddle sleeves 235, 237 will, preferably, additionally have the same curvature as the curvature of the arteries 202 and/or include a portion shaped to the shape of the aneurysm.

Additionally, referring now to FIGS. 1, 14 and 15, the sleeve 210 of the present invention can optionally include a bellows 220 formed therewith and/or attached thereto. More particularly, in one particular embodiment of the invention one or both ends of the sleeve 210 includes a groove or "O"-ring like protuberance for engaging a corresponding "O"-ring like protuberance or groove on a bellows 220. In the example shown in FIGS. 14 and 15, the sleeve 210 includes a groove 212 at one end thereof, which is sized to receive an "O" ring like protuberance 222, formed on the inner wall of the mouth of the bellows 220. This is not meant to be limiting, as it can be seen that the protuberance can be formed on the sleeve 210, with the groove being formed in the inner wall of the mouth or "connector end" 225 of the bellows 220, without deviating from the scope of the present invention. The groove 212 and protuberance 222 interlock or matingly engage to secure the bellows 220 to an end of the sleeve 210, so as to secure the sleeve 210 in place and prevent it from sliding up or down the aorta.

The bellows 220 additionally serves another function. At the very rapid rates the heart is alternately contracting and relaxing (i.e., moving up and down) to pump blood, the bellows 220 permits this movement of the heart without restriction and without the risk of chaffing, scraping, and/or damaging the walls of the heart. Such movement is absorbed with, and/or compensated for by, the folds of the bellows 220. Additionally, a part of the bellows 220 in direct contact with the heart 205 will have a flat surface 227 having the same curvature as the face of the heart 205, thus permitting the heart to move without restriction and without the risk of chaffing, scraping, and/or damaging the walls of the heart.

Note that, although a bellows 220 is described, it is not intended that the invention be solely limited thereto, as a different mechanism can be used to safeguard the heart against a risk of chaffing, scraping, and/or damaging to the walls thereof while the heart 205 is pumping.

In one particular embodiment of the invention, a sleeve, such as the sleeve 110 of FIG. 4 or 210 of FIG. 1, will be constructed as an "inner tube", thus forming a chamber that can be pressurized to different pressures by the doctor or other treating attendant, at will, according to the patient's medical condition at the time of the operation, in order to restrict and/or constrict the aneurysm.

Referring now to FIG. 18, there is shown a chambered sleeve 300, made in accordance with of the present embodiment, which is a double walled sleeve that is placed around the outside of a vessel 100 containing an aneurysm (an aorta, in the instant example). This chambered or double walled sleeve 300, i.e., having an inner wall "I" and an outer wall "O", provides a chamber 305 within the sleeve 300 that can be pressurized, at the doctor's discretion and other health conditions of the patient, including blood pressure related conditions.

Figure 21B:
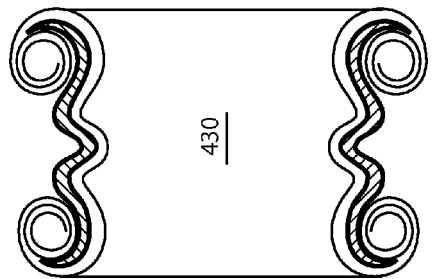
FIG. 21b is a side view of the sleeve portion of FIG. 21, wherein the sleeve portion has been rolled for use and is not yet deployed.
Figure 21C:
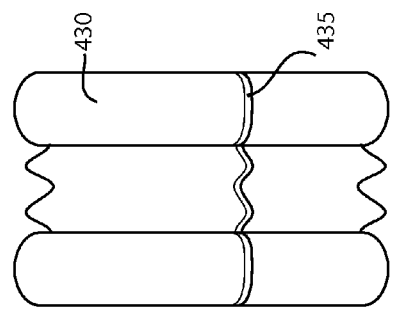
FIG. 21c is a side view of the sleeve of FIG. 21a, wherein the sleeve has been rolled for use.

In practice, the chambered sleeve 300 is installed over the aneurysm in a two-step process. In step one, the sleeve 300 is placed or positioned over the aorta, before the aneurysm, in an initial open and deflated state. See, for example, FIG. 21B. In step two, there are two possible options on how to proceed. In the first option, the locking mechanism 435 on the two lips of the sleeve 300 are interlocked (mated). Thereafter, a pressurized fluid is applied to the sleeve chamber (108 of FIG. 24) to enable the deployment unrolling of the sleeve 300 over the aneurysm. The sleeve is then unrolled and deployed to a point beyond the aneurysm, as determined by the physician. In the second option, the sleeve remains open and a pressurized fluid is applied to the chamber (108 of FIG. 24) to enable the sleeve to deploy over the aneurysm. See, for example, FIG. 29A. After the sleeve has been deployed over and beyond the aneurysm, the locking mechanism 435 of the lips of the sleeve 00 are interlocked (mated). The sleeve is deployed/unrolled in the direction of the blood flow. See, for example, FIGS. 22 and 22A. Being flexible, the sleeve 300 will take the shape, the geometrical configuration, and the curvature of the aorta and the aneurysm.

In particular, the chamber 305 between the inner wall "I" and the outer wall "O" will be pumped with air or fluid from an external air or fluid source 310, via a valve in the sleeve, such as a ball air valve or other type of valve, such that the distance between the two walls "I", "O" will change from the distance "A" in its uninflated state (sleeve 300) to an inflated distance "B" (sleeve 300a), depending on the final pressure, as determined by the physician. Alternately, the sleeve 300 can be deflated or left at the same pressure as during deployment of the sleeve 300, as desired by the physician. In one particular embodiment of the invention, the double walled sleeve 300 is made from a medical grade of plastic and/or a medical grade metal material, or any other medical grade material approved by the FDA or another supervisory authority. In a further embodiment of the invention, the outer wall "O" of the double walled sleeve will be made from a harder and/or thicker material than the inner wall "I" of the double walled sleeve 300.

Figure 24:
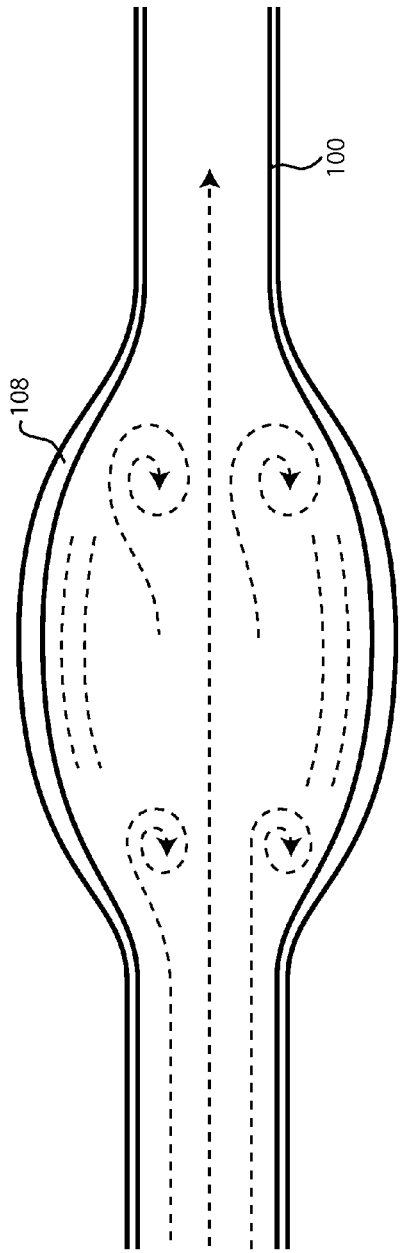
FIG. 24 is a side, cross-sectional view of a vessel containing an aneurysm and showing lines representing the turbulent blood flow therethrough.

Referring now to FIGS. 19-20 and 24, there is shown a "chambered" sleeve 350, made in accordance with one particular embodiment of the invention. In the instant embodiment, the chambered sleeve 350 is formed of two layers 352, 354, wherein the outside wall 352 is made of a harder and thicker material than the inner wall 354. The chambered sleeve 350 can be made in a fashion so that it is able to expand and contract similar to an accordion. When initially inserted over the vessel 100, the chambered sleeve 350 will be in its deflated state, wherein it is collapsed upon itself and deflated, as shown more particularly in FIGS. 20 and 21b.

The collapsed and deflated chambered sleeve 350 will be secured over and around an aneurysm 108 of FIG. 24 (as will be described more particularly herebelow), using the locking mechanism 355. The locking mechanism 355 can be any of the locking mechanisms described herein. However, in one particular embodiment shown in FIGS. 19 and 19a, the locking mechanism 355 is an interlocking male and female dovetail or keystone configuration that is used to secure the interlocking edges of the flat, open sleeve 350 into a tube. Being flexible and inflatable, the chambered sleeve 350, after inflation, will automatically take the shape and curvature of both the vessel 100 and the aneurysm 108.

Thereafter the chambered sleeve 350 can be inflated and pressurized by the physician, by applying an air or other fluid source to the valve 360, if desired. Alternately, the valve 360 can be used to deflate the sleeve 350, as desired. Note that, a single valve 360 can be used to inflate the entire sleeve 350. The physician will then determine the required pressure necessary to allow the aneurysm (aortic or otherwise) to return to approximately its original size (contrast, for example, FIGS. 22-23), and can further inflate the sleeve, deflate the sleeve and/or leave the sleeve at the current pressure, in order to achieve the pressure determined. By equalizing the arterial blood pressure through the aneurysm (108 of FIG. 24), an unobstructed blood flow will occur and will minimize the risk of blood flow turbulence either at the point of entry from the healthy artery into the aneurysm chamber 108, or at the exit from the aneurysm chamber 108 to the other side to the healthy artery 100.

Figure 25:
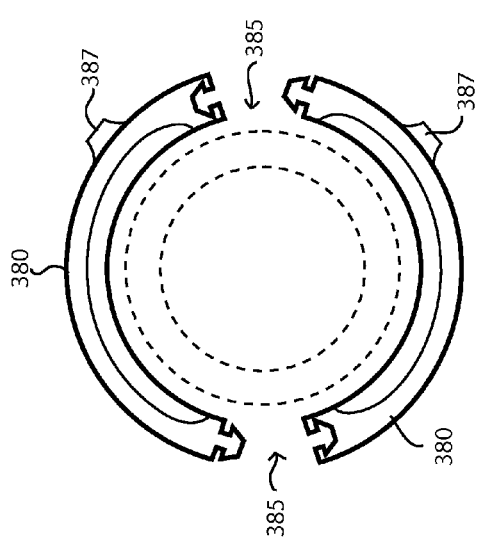
FIG. 25 is an exploded, cross-sectional view of a sleeve made in accordance with a further particular embodiment of the instant invention.
Figure 25A:
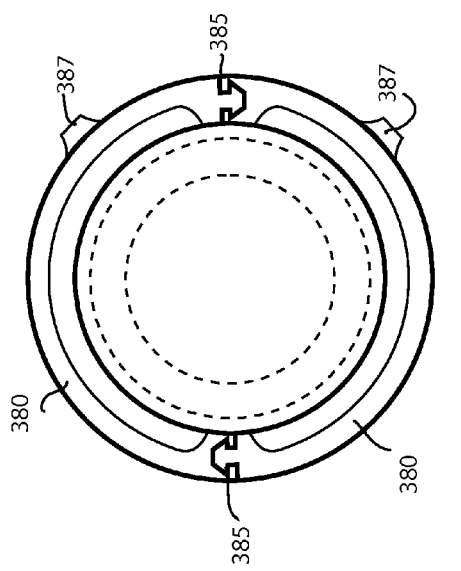
FIG. 25*a* is a longitudinal, cross-sectional view of a sleeve in accordance with one particular embodiment of the invention.
Figure 26:
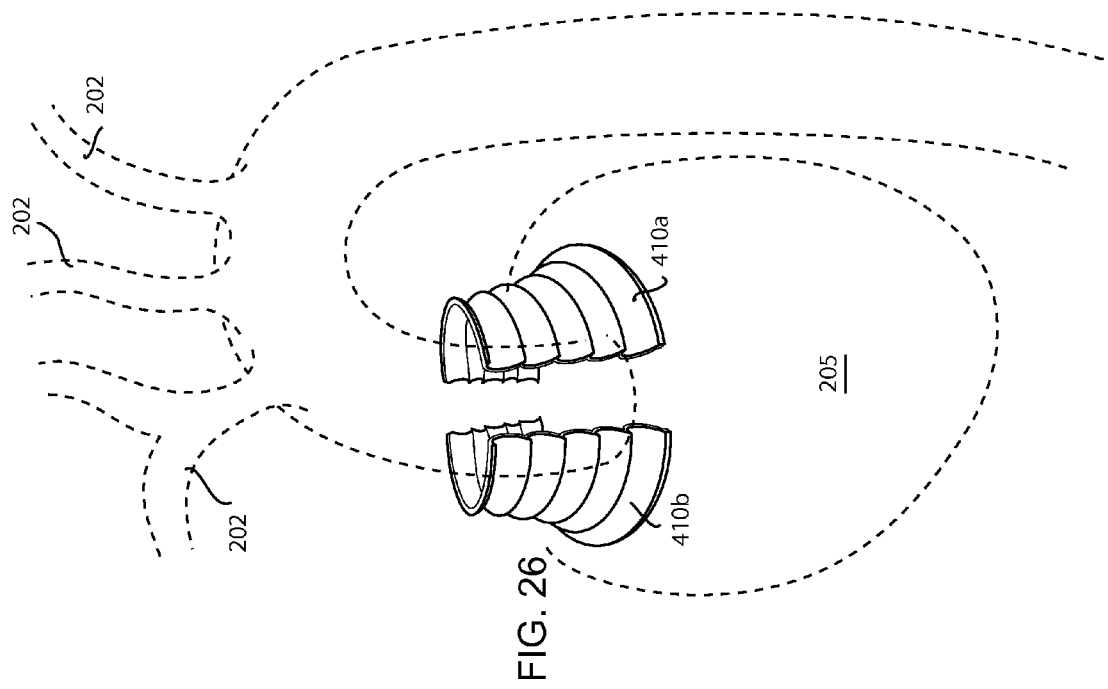
FIG. 26 is an exploded, perspective view of a bellows, shown in a representative placement relative to the heart and aorta, in accordance with one particular embodiment of the present invention.
Figure 34:
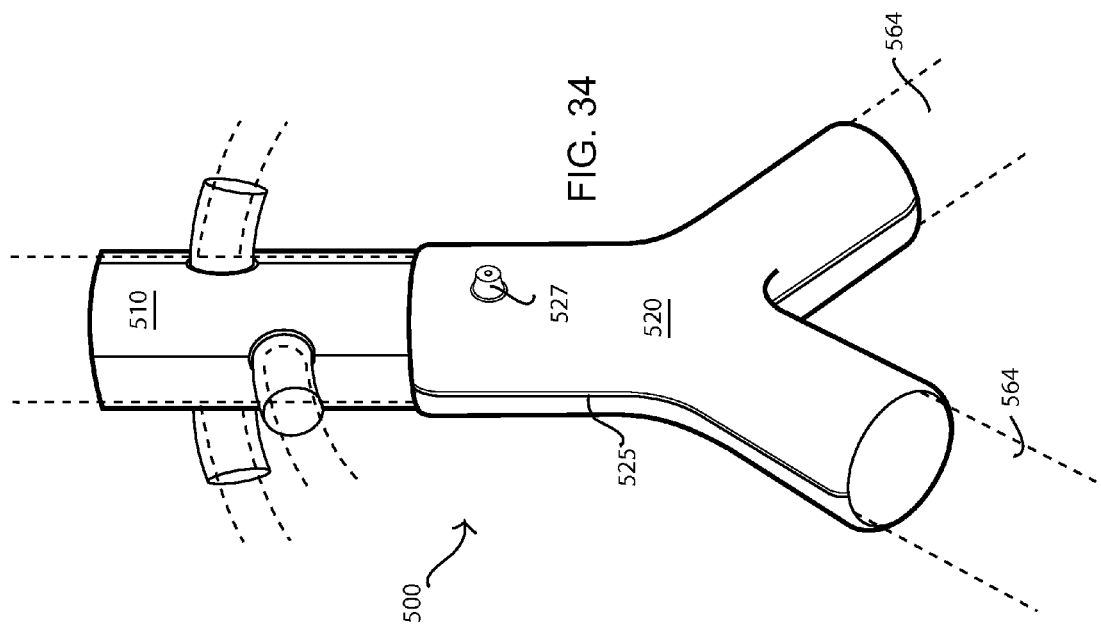
FIG. 34 shows the double-walled sleeve of FIG. 32 deployed and installed, in engagement with the securing and saddle sleeves of FIG. 33, to form a sleeve for constricting and restricting an aneurysm in accordance with one particular embodiment of the present invention, the securing and saddle sleeves being usable at any location necessary to anchor and secure the aneurysm sleeve for constricting and restricting the aneurysm.
Figure 33:
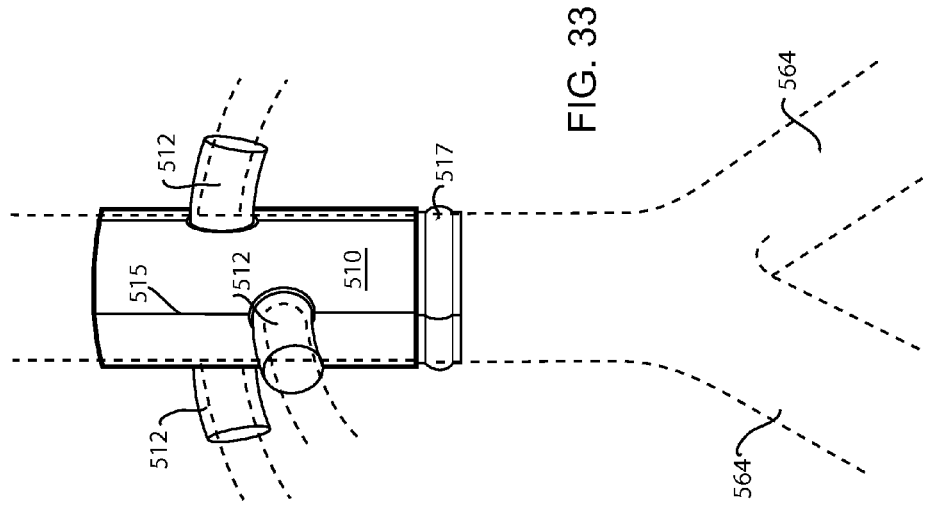
FIG. 33 is a perspective view of a securing sleeve and saddle sleeves for use over smaller arteries, which are provided to anchor and secure the sleeves, for example, the sleeves of FIGS. 4, 6, 7, 8, in such manner as not to allow the sleeves to slide upwards or downwards over the aorta and the aneurysm, while still permitting free pulsating movement (expending and contracting movements) of the aorta with the differential periodic blood pressure.

In another particular embodiment of the invention, the chambered sleeve of the invention can be constructed as two or more parts that are secured together around the vessel containing the aneurysm. For example, as shown more particularly in FIGS. 25 and 25a, the chambered sleeve 350 of FIG. 19 can, instead be constructed from two halves 380 matingly engaged to one another by the locking mechanisms 385, with each half being inflatable via a valve 387. Such a design is particularly useful for treating any of an ascending aortic aneurysm, a descending aortic aneurysm and/or a thoracic aneurysm. In certain instances, such as with an abdominal aortic aneurysm, the sleeve will be made in two halves, in the same fashion as the chambered sleeve 380 of FIGS. 25-25a.

The inflating valves 360, 387 can be of any type of valve useful for such a purpose, including, but not limited to, a ball air valve.

Referring now to FIGS. 19-29b, one particular method of installing a sleeve over an aneurysm in accordance with one particular embodiment of the invention will now be described. In particular, a sleeve in accordance with the instant invention must be installed in a very specific and careful manner, in the direction of blood flow, so as to not cause heart failure, drastic blood pressure changes in the artery or arteries, or significant changes in the blood flow of the artery or arteries. First, a patient is prepped for surgery, in any way deemed appropriate by the surgeon. This can include, among other things, performing procedures to slow down the patient's body metabolism to the greatest extent possible, by cooling down the body temperature. In one particular embodiment of the invention, the patient's body temperature is cooled about 11 percent for every 10 mm Hg rise in central aortic pressure.

Installation Procedure for an Ascending Aortic Aneurysm:

One particular method of installing a sleeve 400, 430 in accordance with one particular embodiment of the present invention will now be described in connection with FIGS. 21-24 and 26. First, as shown more particularly in FIG. 26, a bellows 410 is installed next to the heart. In the embodiment shown, the bellows 410 is made up of two parts 410a and 410b that are matingly engaged using two locking mechanisms, as described hereinabove. Note that this is not meant to be limiting, as the bellows 410 may be made up from a single piece and locking mechanism, or even more than two pieces, as desired.

Once the bellows has been secured next to the heart, the saddle sleeves 422 can be installed and secured over the small arteries 402 coming out of the aorta. The saddle sleeves may be individual securing buttons or saddle sleeves, as described hereinabove in connection with FIGS. 10-12, or may be part of a three branch manifold, as described in connection with FIGS. 9 and 13, as desired by the surgeon. However, in each case, the saddle sleeves (i.e., securing buttons) are secured around a portion of each of the small arteries 402, with a portion straddling or saddling the aorta 200. A further sleeve, securing sleeve 420, is then secured over the manifold or saddling portions of the saddle sleeves 422, in order to hold them in place in their desired location over the aorta. More particularly, the securing sleeve 420 and saddle sleeves 422 anchor the securing sleeve 420 in place relative to the vessels 402. The saddle sleeve 420 includes openings to permit the passage of the saddle sleeves 422 therethrough, and a locking mechanism 425 for locking the securing sleeve 420 over the aorta and the saddle portions or manifold body, to maintain the saddle sleeves 422 in place. The securing sleeve 420, may or may not be inflatable, as required. In the instant embodiment shown, the securing sleeve 420 is not inflatable.

Once sleeves 422, 420 and bellows 410 have been placed and secured, an inflatable sleeve 430 can be secured over the aneurysm 108 and between the bellows and the anchoring combination formed from the securing sleeve 420 overlaying the saddle sleeves 422. Initially, the sleeve 430 will be deflated and open on one side, as shown more particularly in FIG. 21. The sleeve 430 includes an inner surface 430a, which will contact the aneurysm 108, an outer surface 430b, and a locking mechanism 435, having mating edges 435a and 435b, which engage to form the sleeve 430 into a tube, as shown more particularly in FIGS. 21a, 29, 29a and 29b. Additionally, the sleeve 430, in its deflated and opened state, is rolled over onto itself multiple times (like a condom), as shown more particularly in FIG. 21b. At each end, the sleeve 430 has either a groove or an "O" ring type protuberance, or some other type of locking mechanism, as shown more particularly in FIGS. 27 and 28. A corresponding locking structure or mechanism will also be present on the connecting ends of the bellows 410 and the securing sleeve 420.

As shown more particularly in FIGS. 22 and 27, the sleeve 430 is engaged at one end to the bellows 410 by forming the sleeve 430 into a tube over the end of the bellows 410, using the locking mechanism 435, and matingly engaging the "O" ring type protuberance 412 on the bellows 410 with a corresponding groove 432 on the sleeve 430, or vice versa. Thereafter, the sleeve 430 will be unrolled (deployed) under pressure (i.e., having air or another fluid enter an internal chamber of the sleeve 430, via the valve 437 to unroll/deploy the sleeve 430) over the total length of the affected aorta, from the bellow 410 onwards up to the sleeve 420, and locked by mating a groove 434 on the inner surface 430a of the sleeve 430 over an "O" ring type protuberance 421 on the outer surface of the securing sleeve 420 (or vice versa). Compare, for example, FIGS. 22-23, 27 and 28. The unrolling of the sleeve 430, and the progressive engagement of the locking mechanism 435 as it is deployed (see also, for example, FIGS. 29, 29a and 29b) should be performed at a very slow advancing rate and should take several minutes. The initial pressure applied to unroll the sleeve 430 will be less than the final pressure of the sleeve 430, in one particular embodiment of the invention. In another embodiment of the invention, the sleeve 430 will be left at the pressure present in the sleeve once the sleeve 430 has been deployed, which may equal the initial pressure applied to deploy the sleeve 430.

In a further embodiment of the invention, once the sleeve 430 has been deployed under pressure and is in its final form and/or location, the air in the internal chamber may be removed or released, in order to deflate the sleeve 430, and/or to avoid compressing or constricting the blood vessel, if desired. The amount of air left in the chamber after the sleeve 430 has been deployed around the vessel is preferably determined by a physician based on the sleeve materials selected and/or the particular conditions and anatomy of the patient.

Using a device similar to the inflation mechanism used for a sphygmomanometer or "blood pressure cuff", the sleeve 430 will be gently inflated to the required arterial patient blood pressure. For the proper function of any aneurysm device, and so as to not endanger the patient's life, the pressure within the sleeve 430 must equalize the pressure within the aorta. To insure this correct and proper pressure between the sleeve 430 and the aorta, a special blood pressure monitoring device should be provided to measure this pressure through the device of the invention, and the aorta.

Installation Procedure for a Descending and/or Thoracic Aortic Aneurysm:

The same procedure for installing a sleeve over a descending and/or thoracic aortic aneurysm will be basically the same as is described above in connection with the installation of a device over the ascending aortic aneurysm, with the exception that a bellows 410 is not used in connection with a descending/thoracic aortic aneurysm. Referring more particularly now to FIGS. 35-36, in the case of a descending and/or thoracic aortic aneurysm, saddle sleeves 455 are installed in a similar manner as discussed in connection with saddle sleeves 235, 237 or 255 of FIGS. 9-12 and 13, and a securing sleeve 450 is placed there over. However, in association with the descending aorta 106, an inflatable sleeve 460 is connected to the distal end of the securing sleeve 450 (i.e., the end distal from the heart). The sleeve 460 is applied and deployed under pressure over the affected portion of the descending and/or thoracic aorta 106 including the aneurysm 108, in much the same way as was described in connection with the installation of the sleeve 430 of FIGS. 22 and 22a. As noted above, pressure may be applied by introducing air from an air source into the sleeve halves, via a valve (not shown). Additionally, the unrolling of the sleeve 460 starts from the "O"-ring type protuberance 452 on the securing sleeve 450, and moves away there from, so as to ensure that unrolling of the sleeve 460 is effectuated in the natural direction of the blood flow through the aorta. As discussed elsewhere herein, the final pressure in the sleeve 460 may be the same as, greater than or less than the pressure in the sleeve 460 during the unrolling step.

Installation Procedure for an Abdominal Aneurysm:

One particular method of treating an abdominal aortic aneurysm, in accordance with the present invention will now be described. More particularly, referring now to FIGS. 30-34, there is shown one particular embodiment of a sleeve device 500 for use with an abdominal aortic aneurysm. The aneurysm sleeve device 500 has a two part construction wherein a first sleeve or securing sleeve 510 is used to maintain the second sleeve 520 in a desired position relative to the aorta 560 and aneurysm.

Figure 12:
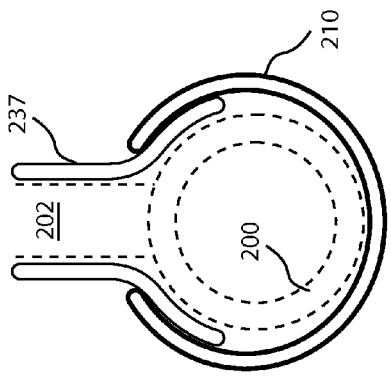
FIG. 12 is a longitudinal, cross-sectional view of a vessel carrying an additional saddle sleeve or securing button, overlaid by a securing sleeve, in accordance with one particular embodiment of the invention.

In use, the securing buttons or saddle sleeves 512 are installed over the small arteries 562 of the abdominal aorta and aneurysm, in much the same way as was described in connection with the saddle sleeves 235, 237 of FIGS. 10, 11 and 12. Alternately, a three branch manifold, as described in connection with FIGS. 9 and 13, could be reconfigured for use with the arteries 562. Once the saddle sleeves 512 and/or manifold containing the saddle sleeves 512 have been placed, a securing sleeve 510 can be closed over a saddle portion of the saddle sleeves 512, to maintain the saddle sleeves 512 in the proper position relative to the aorta and aneurysm, as shown more particularly in FIG. 33.

According to the present particular embodiment of the invention, after installation of the saddle sleeves 512 and the securing sleeve 510 (FIG. 33), the sleeve 520 can be placed and secured over and around the branched portion 564 of the abdominal aorta and the aneurysm. More particularly, a sleeve 520, which, in the presently shown embodiment is made up of two halves 520a and 520b, is placed around the branched portion 564 of the abdominal aorta by connecting the two halves 520a and 520b, using a locking mechanism 525 in the manner discussed hereinabove. Additionally, the sleeve 520 is secured to the securing sleeve 510 by fastening the groove 529 on the sleeve 520 around an "O"-ring like protuberance 517 on the securing sleeve 510, or vice versa. The securing sleeve 510 operates to maintain the sleeve 520 in its desired location.

Figure 21:
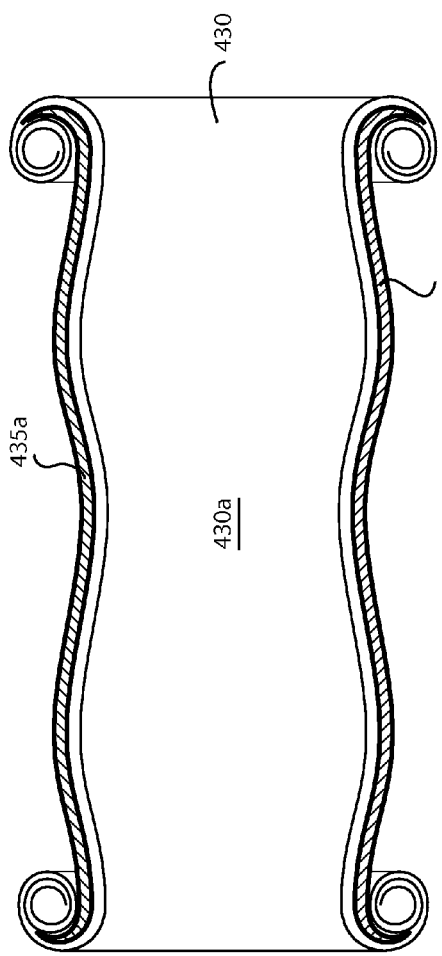
FIG. 21 is a side view of the inside wall of a portion of a sleeve made in accordance with one particular embodiment of the invention.
Figure 21A:
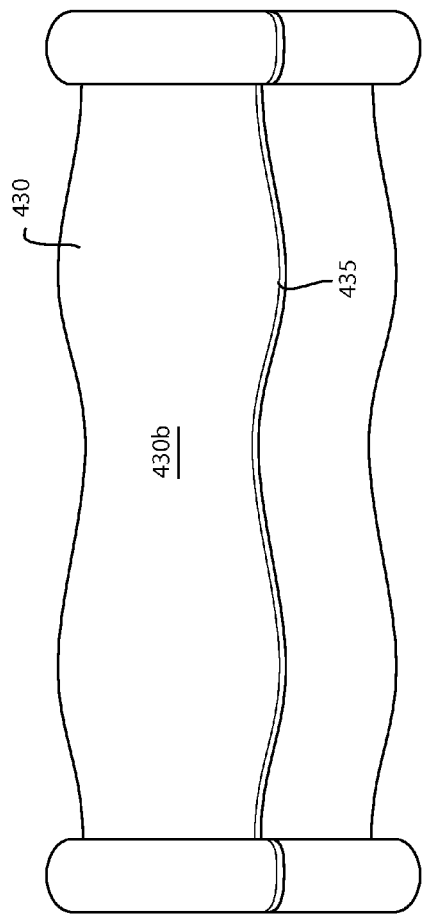
FIG. 21a is a side view of a double-walled sleeve formed from the sleeve of FIG. 21, once it has been deployed (unrolled) and closed.
Figure 23:
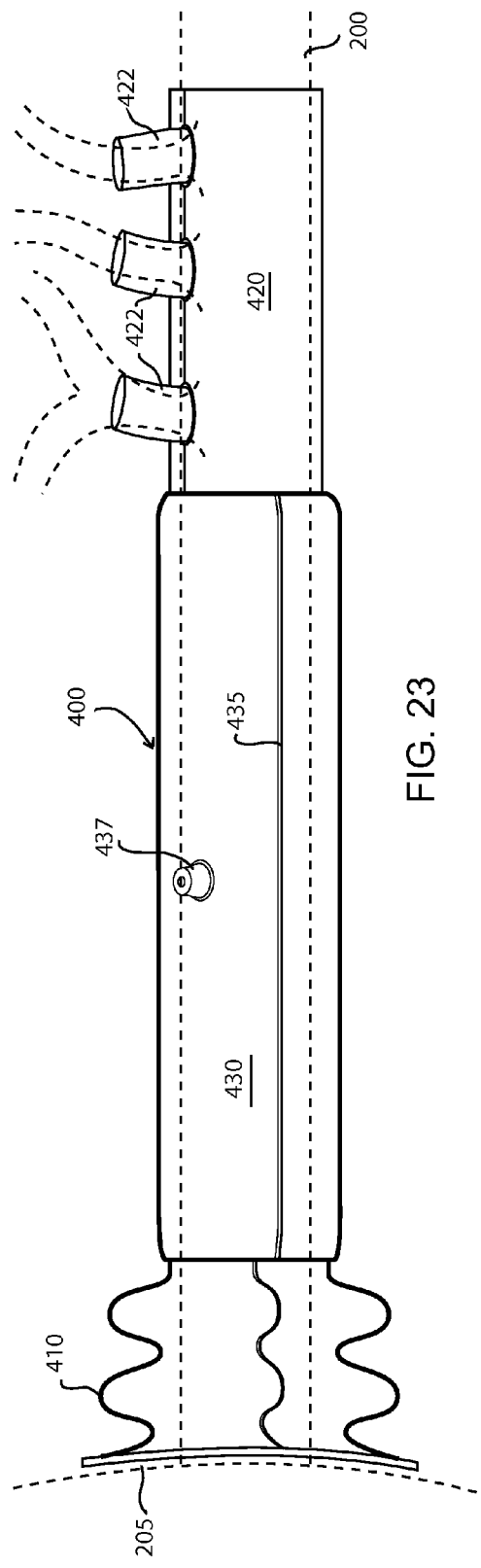

As described in connection with FIGS. 21-23, hereinabove, the sleeve 520, and its respective halves 520a and 520b may be rolled for insertion. However, once the sleeve halves 520a and 520b are secured over the "O"-ring like protuberance 517, and to one another at the end proximal to the protuberance 517, the sleeve halves may be unrolled, under pressure, and progressively, matingly engaged to one another until the sleeve 520 extends over the total length of the affected portion of the aorta and the aneurysm (i.e., downwards from the connecting edge of the securing sleeve 510). Pressure may be applied by introducing air from an air source into the sleeve halves 520a and 520b, via the valves 527.

More particularly, the two halves 520a, 520b of the sleeve 520 will come deflated. One half 520a or 520b will be placed below the affected abdominal aortic aneurysm area, while the other half 520a or 520b will be placed above the affected abdominal Aneurysm area and unrolled slowly over the aneurysm (i.e., by introducing air into a chamber of each half 520a, 520b to unroll the respective half). The bottom half will serve as counter support resistance for the top half. See, for example, FIGS. 30-32.

The two halves 520a and 520b of the sleeve 520 will be snapped or locked and secured against each other and over "O"-ring type protuberance 517 of the securing sleeve 510 and, thereafter the two halves 520a and 520b will be inflated simultaneously at a very low rate of inflation. The unrolling of the sleeve 520 should be performed at a very slow advancing rate. The initial pressure applied to deploy the sleeve 520 in the direction of the blood flow will be less than the final pressure of the sleeve 520. Alternately, as discussed elsewhere herein, the final pressure in the sleeve halves 520a, 520b may be the same as or less than the pressure in the sleeve halves 520a, 520b during unrolling.

It is important to note that, in each of the foregoing cases, the inflatable sleeve should be deployed over any aneurysm in the direction of the natural blood flow through the vessel.

Figure 37:
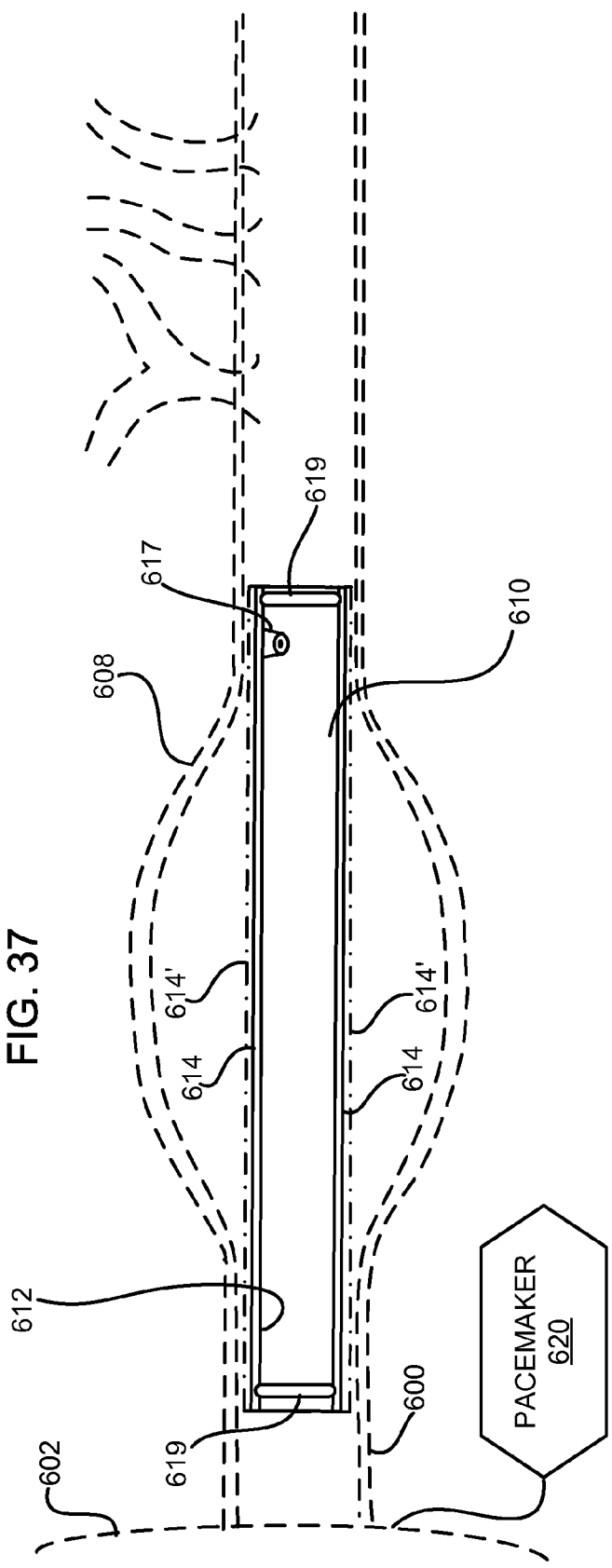
FIG. 37 is a side, cut-away view of a double-walled or inflatable sleeve useful inside the ascending aorta for providing a bypass through an ascending, descending, thoracic or abdominal aortic aneurysm, in accordance with one particular embodiment of the present invention.

Referring now to FIG. 37, there is shown a further embodiment of an inflatable sleeve for treating an aneurysm in accordance with the instant invention. In the instant embodiment, a double-walled or inflatable sleeve 610, as described herein, is disposed inside of the ascending aorta, and located so as to bypass the ascending aortic aneurysm 608, proximal to the heart 602. The sleeve 610, which may be a double-walled tube formed by an inner wall 612 and an outer wall 614, sealed together in an airtight manner. A valve 617 is disposed inside of the sleeve 610. The valve 617 can be connected to an air source (not shown), so as to inflate the double-walled sleeve 610. As air from the air source enters the sleeve, the outer wall of the tube 614a extends away from the inner wall, as shown in dashed line. Thus inflated, the sleeve 610, blood flows through the sleeve 610, thus bypassing the walls of the aneurysm. The turbulent blood flow through the aneurysm is reduced and, eventually, the aneurysm 608 will shrink.

The sleeve 610 may be secured inside the vessel at the point of the aneurysm, as desired. In one preferred embodiment of the invention, the sleeve 610 is not stitched inside the aorta 600, but rather is held in place by gluing, clamping or another type of fixation, and/or by using any of the sleeves of FIGS. 4, 6, 7, 8, 20, 21a inflated over only at the "O" 619 of FIG. 37. In a further embodiment of the invention, the sleeve 610 is secured in place by magnets 619, which are held in place by an electromagnetic field generated by a pacemaker 620 that is placed in the chest or abdomen of a patient, for regulating the heart 602. Alternately, magnets 619 of FIG. 37 may be permanent magnets used to secure the sleeve 610 in a desired place.

Figure 38:
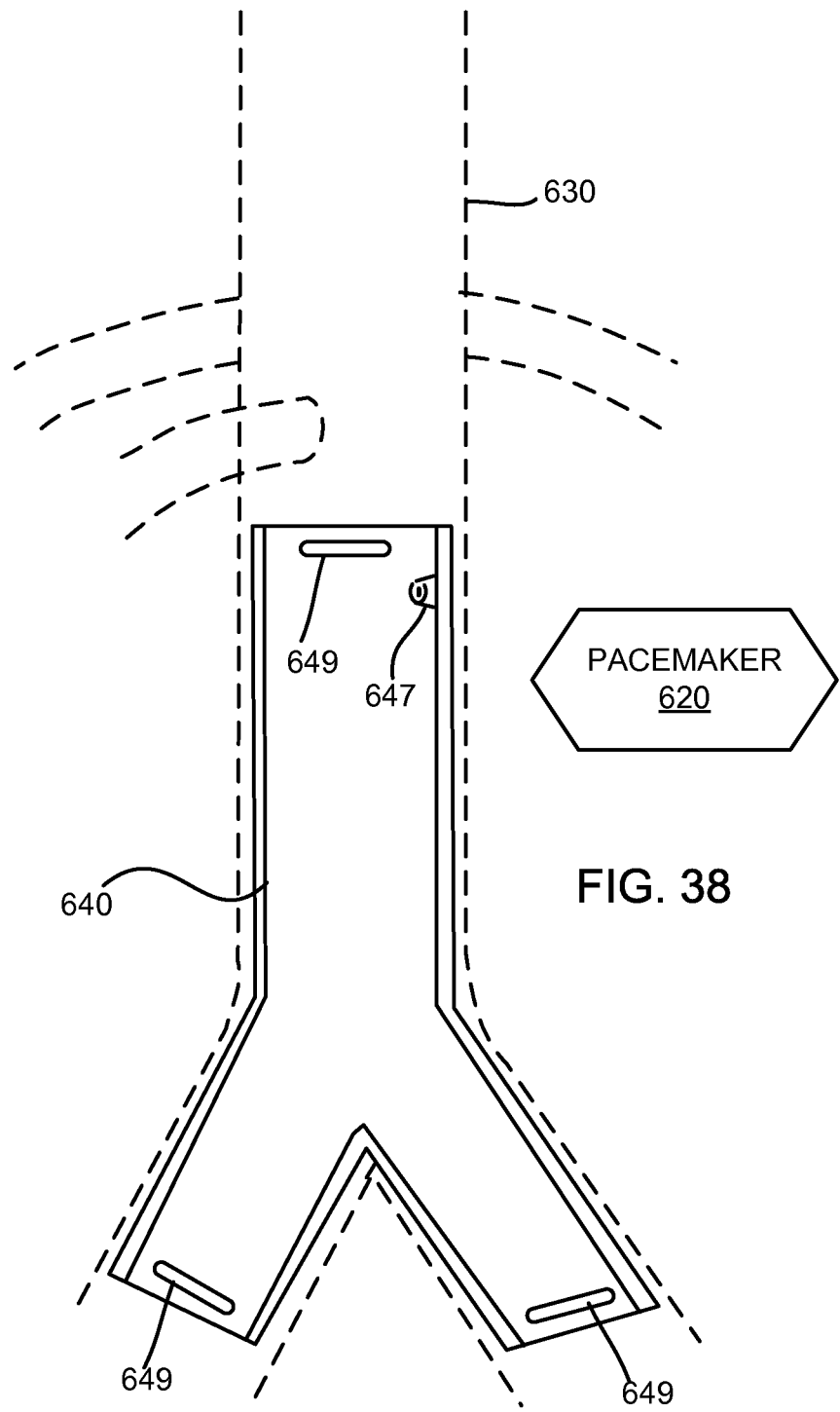
FIG. 38 is a side, cut-away view of a double-walled or inflatable sleeve useful inside the abdominal aorta for providing a bypass through an abdominal aortic aneurysm, in accordance with one particular embodiment of the present invention.

Although shown in the ascending aorta in FIG. 37, it should be understood that a double-walled sleeve (like the double-walled sleeve 610) can be adapted for use in the descending, thoracic and/or the abdominal aorta. For example, referring now to FIG. 38, a double-walled sleeve 640 having a valve 647 therein can be made in the form of a forked tube, for placement in the branches of the abdominal aorta 630, and thus, bypassing an abdominal aortic aneurysm in the wall thereof. As with the double-walled sleeve 610, such a double walled sleeve 640 can be fixed inside the descending, thoracic and/or abdominal aorta by gluing, clamping, or some other method of fixation. In one particular embodiment of the invention, such a double-walled sleeve is secured in place by magnets 649 that are held in place by an electromagnetic field generated by a pacemaker 620 that is placed in the chest or abdomen of a patient, as described hereinabove, or with permanent magnets. In a further alternate embodiment of the invention, the double-walled sleeve 610, 640 can include non-inflatable portions at each end that can be stitched, stapled and/or clipped to the walls of the vessel, without violating the integrity of the airtight inner chamber of the sleeve. Note that the double-walled sleeves 610 and 640, although disposed inside of the vessel, rather than external to the vessel, may be provided in rolled form (as described in connection with sleeve 430, 460 and halves 520a and 520b) and deployed inside of the vessel by applying pressure to the rolled sleeve by the introduction of air into the chamber between the double-walls of the sleeve 610, 640.

Figure 39A:
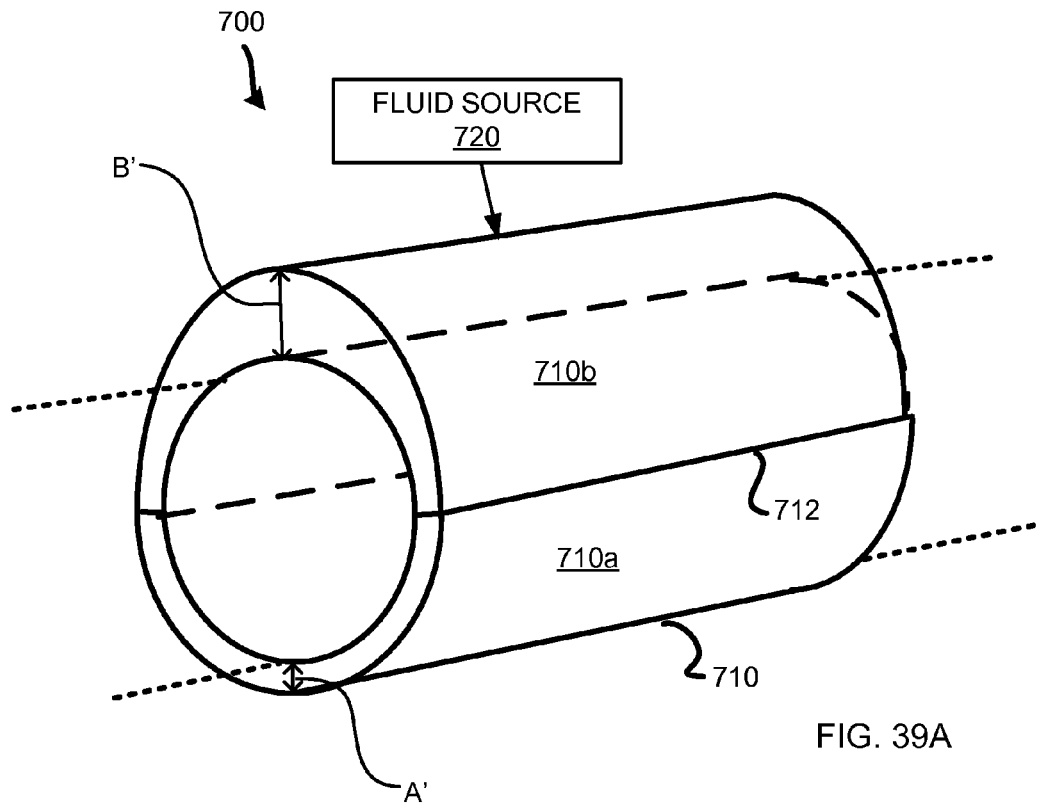
FIG. 39A is a perspective view of a partially inflatable sleeve made in accordance with one particular embodiment of the present invention.
Figure 39B:
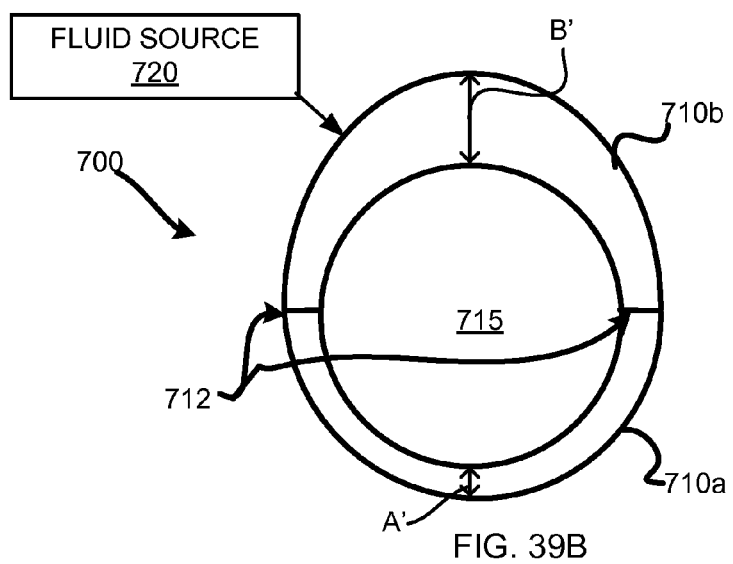
FIG. 39B is a cross-sectional front plan view of a partially inflatable sleeve made in accordance with one particular embodiment of the present invention.

Referring now to FIGS. 39A and 39B, there is shown another embodiment of a system 700 utilizing a chambered or double walled sleeve 710, which may be used in accordance with the present invention. The chambered sleeve 710 resembles the chambered sleeve 300 of FIG. 18, and includes an inner wall and an outer wall. However, the chambered or double walled sleeve 710, instead of being inflatable over a large portion of its circumference, is inflatable over a smaller portion of the device 710. In particular, rather than including a fully inflatable sleeve, the sleeve 710 includes an inflatable pocket into which a pressurized fluid may be injected by the fluid source 720. Thus, one portion of the sleeve 710 remains at the uninflated thickness A', while a second portion (i.e., a fluid-filled pocket of sleeve 710) is inflated to a second, greater thickness B'.

In the particular embodiment shown, the sleeve 710 includes two portions 710a and 710b, mated by locking mechanism 712 around the vessel located in the chamber 715 formed by the mating of the locking mechanism 712. In the embodiment shown, the portion 710b is inflatable by a fluid source 720 (preferably, an air source), while the portion 710a is not. In this way, the physician can determine whether one portion of the underlying vessel should be subjected to a different pressure than the other (for example, the aneurysm side being inflated to a greater pressure than the non-aneurysm side of the vessel, or vice-versa). Although a two part device is shown in FIGS. 39A and 39B, this is not meant to be limiting, as it should be understood that a single part device including a fluid chamber formed in an isolated and/or limited part of the sleeve, only, could be made and used, as desired. In one particular embodiment of the invention, a double chambered sleeve 710 including a single locking mechanism 712 is formed having the chamber size limited by a thermal weld or other fabrication technique to delimit the fillable portion of the chamber (between the inner and outer walls) to a predetermined size less than the entire usable area of the sleeve 710. The sleeve 710 may be installed in accordance with any of the methods described previously herein. Additionally, a sleeve 710 of this type is particularly suited for application on the ascending aorta.

It should be understood from the foregoing, that the sleeves of the present invention can be applied in or around a particular blood vessel adjacent a desired location by a physician, manually, or with robotic assistance.

Although the invention is illustrated and described herein, various modifications and structural changes may be made therein without departing from the spirit of the invention and within the scope and range of equivalents of the claims.

I claim:

1. A method of deploying a sleeve relative to a blood vessel, the method comprising the steps of:
   a) providing a double-walled sleeve including an internal chamber between two walls of the double-walled sleeve, the double-walled sleeve being rolled over onto itself;
   b) introducing the double-walled sleeve, while still rolled over onto itself, into the body adjacent to a blood vessel;
   c) deploying and implanting the double-walled sleeve at a desired location in or around the blood vessel by introducing a fluid into the internal chamber between the two walls of the double-walled sleeve to unroll the double-walled sleeve as fluid is introduced into the internal chamber, such that the double-walled sleeve is in contact with the vessel.

2. The method of claim 1, wherein said fluid is air from a source of pressurized air.

3. The method of claim 1, wherein the double-walled sleeve is deployed adjacent to the blood vessel at a portion of the blood vessel containing an aneurysm.

4. The method of claim 1, wherein, in the deploying step, the double-walled sleeve is unrolled inside the blood vessel.

5. The method of claim 1, wherein, in the deploying step, the double-walled sleeve is unrolled external to the blood vessel.

6. The method of claim 5, wherein the double-walled sleeve is provided deflated and opened, the method further including the step of, securing the double-walled sleeve around the blood vessel using a locking mechanism on the double-walled sleeve.

7. The method of claim 6, wherein the securing step is performed during the deploying step.

8. The method of claim 7, wherein the double-walled sleeve is secured around a portion of the blood vessel including an aneurysm.

9. The method of claim 7, wherein, after the deploying and securing steps, at least a portion of the fluid introduced into the chamber in the deploying step is removed from the chamber.

10. The method of claim 5, wherein the double-walled sleeve includes a first sleeve portion and a separate, second sleeve portion, and wherein the method further includes a securing step including the steps of:
    securing the first sleeve portion around the blood vessel; and
    securing the second sleeve portion around a portion of the blood vessel and fixedly engaging the second sleeve portion to the first sleeve portion.

11. The method of claim 10, wherein the securing step is performed during the unrolling step.

12. A method of deploying a sleeve relative to a blood vessel containing an aneurysm, the method comprising:
    providing the sleeve including an inner wall and an outer wall, the inner wall and outer wall arranged relative to each other to form an airtight chamber there between, the sleeve being in a rolled state, wherein it is rolled over onto itself in a direction along the length of a longitudinal axis through the sleeve;
    disposing the sleeve, while in the rolled state, into the body adjacent a portion of a blood vessel containing an aneurysm; and
    deploying the sleeve, while adjacent the portion, by introducing a fluid into the airtight chamber.

13. The method of claim 12, wherein the inflatable sleeve is configured for placement inside of the blood vessel containing the aneurysm.

14. The method of claim 12, wherein the sleeve is configured for placement over and around an exterior surface of the blood vessel.

15. The method of claim 14, wherein in the providing step, the sleeve is additionally provided deflated and opened.

16. The method of claim 15, wherein the sleeve includes a locking mechanism for fixing the sleeve in tubular form around the portion of the blood vessel.

17. The method of claim 16, wherein the locking mechanism is an interlocking tongue and groove configuration.

18. The method of claim 16, wherein the unrolling step further includes locking the locking mechanism for fixing the sleeve in tubular form while progressively deploying the sleeve around the portion of the blood vessel including the aneurysm.

19. The method of claim 18, wherein the fluid is air and the method further includes the step of connecting the sleeve to an air source.

20. The method of claim 19 wherein the final pressure in the sleeve is different from the pressure in the sleeve at a conclusion of the deploying step.

\* \* \* \* \*